United States Patent
Wang et al.

(10) Patent No.: US 11,382,929 B2
(45) Date of Patent: Jul. 12, 2022

(54) COMPOSITIONS AND METHODS TO TREAT DISEASE

(71) Applicant: REGENTS OF THE UNIVERSITY OF MINNESOTA, Minneapolis, MN (US)

(72) Inventors: Chun Wang, Minneapolis, MN (US); Samuel Hanson, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/913,046

(22) Filed: Jun. 26, 2020

(65) Prior Publication Data
US 2020/0405746 A1 Dec. 31, 2020

Related U.S. Application Data

(60) Provisional application No. 62/868,628, filed on Jun. 28, 2019.

(51) Int. Cl.
*A61K 31/785* (2006.01)
*A61K 31/704* (2006.01)
*A61P 35/00* (2006.01)
*A61K 31/727* (2006.01)

(52) U.S. Cl.
CPC .......... *A61K 31/785* (2013.01); *A61K 31/704* (2013.01); *A61K 31/727* (2013.01); *A61P 35/00* (2018.01)

(58) Field of Classification Search
CPC .................................................. A61K 31/704
See application file for complete search history.

(56) References Cited

PUBLICATIONS

Weihang Ji, Synthetic polymers with well-defined structures for DNA vaccine delivery and cancer therapy, Retrieved from the University of Minnesota Digital Conservancy, Nov. 2003 (Year: 2003).*
Young Hee Choi, ABC Transporters in Multidrug Resistance and Pharmacokinetics, and Strategies for Drug Development, Curr Pharm Des. 2014 ; 20(5): 793-807 (Year: 2014).*
Holohan, C , et al., "Cancer drug resistance: an evolving paradigm", Nat Rev Cancer 13(10), 714-726 (2013).
Kabanov, A , et al., "Pluronic block copolymers for overcoming drug resistance in cancer", Adv Drug Deliv Rev 54(5), 759-779 (2002).
Kesharwani, S , et al., "Overcoming multiple drug resistance in cancer using polymeric micelles", Expert Opin Drug Deliv 15(11), 1127-1142 (2018).
Khamisipour, G , et al., "Mechanisms of tumor cell resistance to the current targeted-therapy agents", Tumour Biol 37(8), 10021-10039 (2016).
Tang, R , et al., "Block copolymer micelles with acid-labile ortho ester side-chains: Synthesis, characterization, and enhanced drug delivery to human glioma cells", J Control Release 151(1), 18-27 (2011).

* cited by examiner

*Primary Examiner* — Mark V Stevens
*Assistant Examiner* — Alparslan Asan
(74) *Attorney, Agent, or Firm* — Viksnins Harris Padys Malen LLP

(57) ABSTRACT

Disclosed herein are compositions comprising a membranolytic polymer or a salt thereof and a chemotherapeutic agent or a salt thereof and compositions comprising a membranolytic polymer or a salt thereof and a shielding polymer or a salt thereof. Also disclosed are methods and uses for treating diseases such as cancer with these compositions.

8 Claims, 17 Drawing Sheets

COMPOSITIONS AND METHODS TO TREAT DISEASE

CROSS-REFERENCE TO RELATED APPLICATION

This application claims priority to U.S. Provisional Application No. 62/868,628 that was filed on Jun. 28, 2019. The entire content of the application referenced above is hereby incorporated by reference herein.

BACKGROUND OF THE INVENTION

There is a large number of anticancer agents that are being used on the market and many more are being developed. These agents range from small molecular chemotherapeutic drugs, to peptides, proteins (including antibodies), antibody-drug conjugates, nucleic acids, oncolytic bacteria and viruses. An emerging trend in cancer drug development is the so called "targeted therapies". Such drugs engage specific molecular targets in cancer cells. Examples include Gleevec (a small molecule) and Herceptin (an antibody). While these drugs can work exceedingly well, there are some drawbacks. First, they are only effective in certain subpopulations of patients whose tumors bear certain specific markers. They are ineffective in other patients whose tumors are "negative" of such biomarkers or molecular targets. Second, under the selective pressure of the drugs, cancer cells may evolve a number of mechanisms to confer resistance to a wide range of drugs, rendering them ineffective. Nonspecific killing of cancer cells, such as lysing the plasma membrane of cancer cells, does not have such limitations because any cells, regardless of their phenotype, are susceptible to such destruction, as long as the membrane lytic agents can be made to avoid harming noncancer cells. This in principle can be achieved using methods of drug modification (prodrug approach) and targeted drug delivery systems.

The literature contains reports on antimicrobial peptides and protein (toxins) derived from natural sources or de novo designed, and some have been investigated as potential anticancer drugs. One example is melittin, a peptide found in bee venom. These toxins kill cancer cells through disrupting the cell membrane and damaging mitochondria, leading to cell death. However, they are also toxic to healthy tissues. They are also unstable in vivo due to proteolysis. There are reports on using certain nanocarriers to improve the specificity and safety of these peptides. There are also reports that discuss the use of biocidal polymers as disinfectants. Many synthetic polymers are known to have antimicrobial (antibacterial or antiviral) properties. These polymers kill microbes often through membrane lysis; therefore, many of these polymers kill bacteria and human cells alike. These polymers are often screened for selectivity in killing microbes but sparing mammalian cells, so that they can be safely used as antimicrobial agents. If a polymer is found to exhibit high toxicity toward human cells, it is deemed unsuitable as an antimicrobial. It is known that certain polymers have intrinsic anticancer effects. Some of these polymers have been shown to be directly toxic to cancer cells, while others have either antiangiogenic properties or immunostimulatory properties. However, the potential of such polymers as anticancer agents appears to have been demonstrated in cell culture studies and in a few cases of in vivo studies. However, antitumor response was weak and systemic toxicity was also a concern.

Accordingly, there is a need for new anticancer agents including agents such as polymeric agents (e.g., synthetic or natural) and for methods to treat cancer using such agents. There is also a need for agents that can treat cancer by disrupting cancer cell membranes and that may also have lowered toxicity to non-cancer cells.

A large number of current anticancer drugs are small molecules that must enter cancer cells to reach their targets intracellularly. Examples include targeted therapeutics and conventional chemotherapeutics such as the anthracyclines, a family of compounds that include doxorubicin (Dox), a widely used drug to treat many types of cancers. Dox kills proliferating cells by intercalating into the genomic DNA and by inhibiting the activity of topoisomerase I, thereby interrupting DNA replication. The water-soluble form of Dox is a salt of hydrochloric acid (HCl), which by itself can be internalized into cells and accumulates in the cell nucleus to some degree, but the internalization can be greatly attenuated in cancer cells that are resistant, and the efficacy of Dox can thus be greatly diminished.

Cancer cells often develop resistance to specific drugs or a class of drugs (multi-drug resistance, MDR), rendering these drugs ineffective. There are multiple mechanisms that underlie the MDR phenotype of cancer cells. One of the major mechanisms is the efflux pumps in the cell membrane, which harvest the energy of ATP hydrolysis to pump drug molecules from the intracellular side of the membrane to the extracellular space, thus saving the cancer cell from destruction. MDR cells are therefore difficult to eradicate and are responsible for cancer recurrence after chemotherapy. Moreover, the so called "cancer stem cells" are also multi-drug resistant. There is much effort currently in targeting drugs to destroy cancer stem cells, but success is limited. In the case of Dox, resistant cells survive by limiting the intracellular and intranucleus concentrations of Dox.

Polymers have been used as drug carriers to overcome MDR in cancer cells. Several strategies have been explored. For instance, polymer/drug particles and conjugates enter cells through endocytosis, thus bypassing the membrane efflux pumps (such as P-glycoproteins) and resulting in high levels of drug accumulation in the cytoplasm and nucleus. Another example includes certain polymers that interfere with the activity of the efflux pumps while a third example includes polymers that deliver inhibitors of efflux pumps.

Accordingly, there is a need for new compositions and methods that treat cancer including compositions that deliver chemotherapeutic agents to cancer cells in manner that attenuates the efflux of the agent by the cancer cell.

SUMMARY OF THE INVENTION

Compositions disclosed herein exhibit anticancer activities.

Accordingly, one embodiment provides a composition comprising:

(a) a membranolytic polymer or a salt thereof, and (b) a shielding polymer or a salt thereof, or a chemotherapeutic agent or a salt thereof.

One embodiment provides a composition comprising: (a) a membranolytic polymer or a salt thereof, and (b) a shielding polymer or a salt thereof.

One embodiment provides a composition comprising: (a) a membranolytic polymer or a salt thereof, and (b) a chemotherapeutic agent or a salt thereof.

One embodiment provides a composition comprising: (a) a membranolytic polymer or a salt thereof, (b) a shielding polymer or a salt thereof, and (c) a chemotherapeutic agent or a salt thereof.

One embodiment provides a composition as described herein further comprising a pharmaceutically acceptable excipient.

One embodiment provides a method to treat cancer in mammal (e.g., a human) in need thereof comprising administering to the mammal a composition as described herein.

One embodiment provides a composition as described herein for use in medical therapy.

One embodiment provides a composition as described herein for the therapeutic treatment of cancer in an animal (e.g., a human).

One embodiment provides the use of a composition as herein for the preparation of a medicament for the therapeutic treatment of cancer in an animal (e.g., a human).

The invention also provides processes and intermediates disclosed herein that are useful for preparing compositions described herein.

BRIEF DESCRIPTION OF THE FIGURES

FIG. 5A shows tumor volume, FIG. 5B shows tumor weight, and FIG. 5C shows dimensions of tumors. FIG. 5D demonstrates that heparin/PAHM nanoparticles showed no apparent toxicity judging from constant body weight.

FIG. 6A shows tumor volume, FIG. 6B shows tumor volume at day 12, FIG. 6C shows tumor weight at day 12 and FIG. 6D shows dimensions of tumors. For FIGS. 6B and 6C, the first bar in each set is Heparin only and the second bar in each set is Heparin/PAHM. FIG. 6E demonstrates that there was no significant influence on mouse body weight.

FIG. 9A shows at a fractional affect greater than 0.4 (i.e., 60% cell viability), the combination is synergistic as shown by combination index (CI)<0.9.

FIG. 10A shows at a fractional affect greater than 0.4 (i.e., 60% cell viability), the combination is synergistic as shown by combination index (CI)<0.9.

DETAILED DESCRIPTION

Membranolytic Polymer

Figure 1:
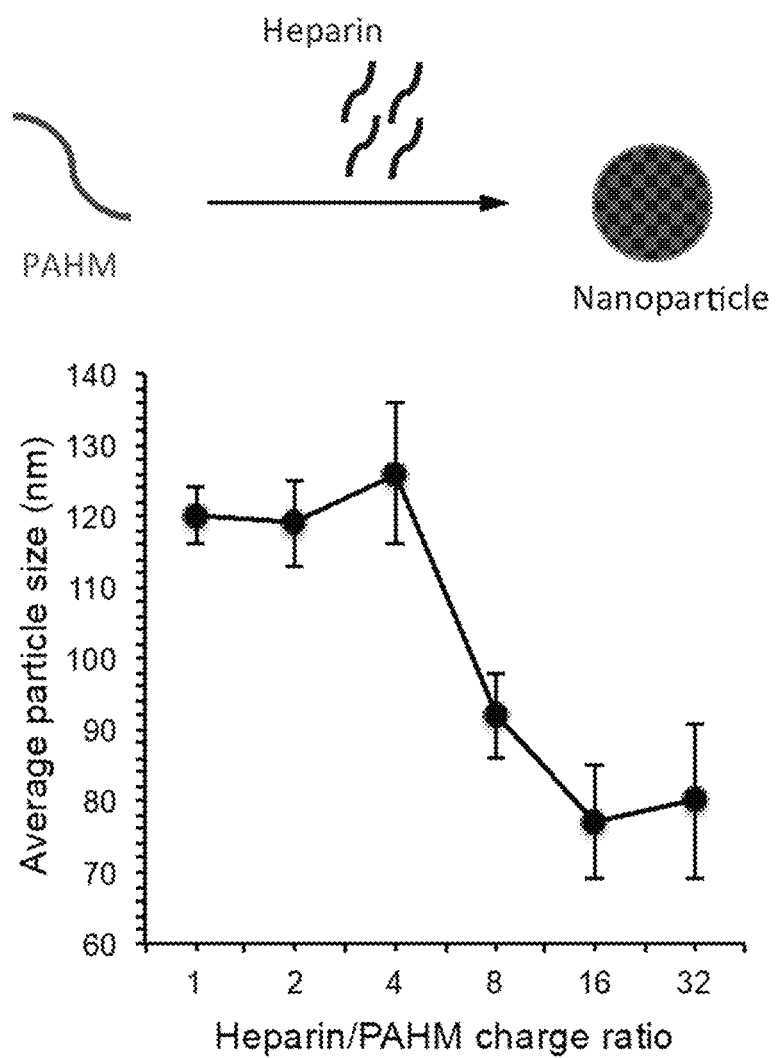
FIG. 1 shows nano-complex formation and dependence of charge ratio.

The term "membranolytic polymer" as used herein refers to any polymer (e.g., natural or synthetic) that alters the function and/or structure and/or integrity of a cell membrane (e.g., the cell membrane of a cancer cell). The membranolytic polymer can alter the function and/or structure and/or integrity of a cell membrane in different ways including but not limited to lysis of the cell membrane leading to cell death (e.g., apoptotic cell death), making the cell membrane more permeable (increasing the permeability of the membrane) to other agents (e.g., chemotherapeutic agent (anticancer drugs) or causing pore formation in the cell membrane. Membranolytic agents are particular membrane-active agents that cause cell membrane disruption. For example, a membranolytic polymer may make the cell (e.g., a cancer cell) more permeable to a chemotherapeutic agent thereby allowing sufficient accumulation of the chemotherapeutic agent in the cell. This is important for cells which have efflux pumps that effectively limit or decrease the amount of chemotherapeutic agent in the cell via active removal (efflux) of the agent. Thus, the membranolytic polymer overcomes or attenuates the action of efflux pumps and provides for enhanced uptake of the chemotherapeutic agent by the cancer cell. The membranolytic polymer can be a natural polymer or a synthetic polymer. In one embodiment the membranolytic polymer is a synthetic polymer.

In one embodiment the membranolytic polymer is a "cationic" polymer. Cationic polymers are polymers that have a positive charge. The positive charge is generally on the core structure of the polymer with the functional group (moiety) bearing the positive charge (positively charged group) covalently bonded to polymer. It is to be understood the positively charged group will be associated with a negatively charged counterion (such as a negatively charged group of a shielding polymer). Generally, the negatively charged counterion will not be covalently bonded to the core of the polymer. In one embodiment the cationic polymer comprises one or more amine groups. In on embodiment one or more of the amine groups is positively charged.

In one embodiment the membranolytic polymer comprises monomers, wherein one or more of the monomers comprise one or more amines. In one embodiment the membranolytic polymer comprises monomers wherein each monomer comprises one or more amine groups. In one embodiment the membranolytic polymer comprises two or more repeat monomers. In one embodiment the membranolytic polymer is a homopolymer.

In one embodiment the membranolytic polymer comprises one or monomers of formula I:

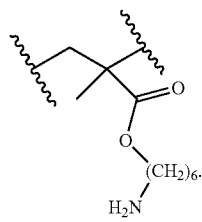

I

In one embodiment the membranolytic polymer is a homopolymer comprising monomers of formula I:

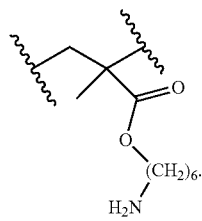

I

In one embodiment the membranolytic polymer comprises poly(6-amino-1-hexyl methacrylate) (PAHM) or a salt thereof. In one embodiment the membranolytic polymer consists of poly(6-amino-1-hexyl methacrylate) (PAHM) or a salt thereof. In one embodiment the membranolytic polymer consists essentially of poly(6-amino-1-hexyl methacrylate) (PAHM) or a salt thereof. In one embodiment the membranolytic polymer is poly(6-amino-1-hexyl methacrylate) (PAHM) or a salt thereof.

In one embodiment the membranolytic polymer has a molecular weight of at least about 1000. In one embodiment the membranolytic polymer has a molecular weight of at least about 2000. In one embodiment the membranolytic polymer has a molecular weight of at least about 5000. In one embodiment the membranolytic polymer has a molecular weight of at least about 10,000. In one embodiment the membranolytic polymer has a molecular weight of at least about 20,000. In one embodiment the membranolytic polymer has a molecular weight of at least about 30,000. In one embodiment the membranolytic polymer has a molecular weight of at least about 50,000.

In one embodiment the membranolytic polymer has a molecular weight of less than about 50,000. In one embodiment the membranolytic polymer has a molecular weight of less than about 30,000. In one embodiment the membranolytic polymer has a molecular weight of less than about 20,000. In one embodiment the membranolytic polymer has a molecular weight of 20,000±15,000.

In one embodiment the membranolytic polymer is a membrane-active polymer that causes cell membrane disruption. In one embodiment the membranolytic polymer comprises one or more monomers of amino alkyl acrylate (e.g., amino-$C_2$-$C_{10}$ alkyl acrylate). In one embodiment the membranolytic polymer comprises one or more monomers of amino alkyl methacrylate (e.g., amino-$C_2$-$C_{10}$ alkyl methacrylate). In one embodiment the membranolytic polymer is a copolymer comprising one or more monomers of amino alkyl acrylate (e.g., amino-$C_2$-$C_{10}$ alkyl acrylate) and one or more monomers of alkyl acrylate (e.g., $C_2$-$C_{10}$ alkyl acrylate). In one embodiment the membranolytic polymer is a copolymer comprising one or more monomers of amino alkyl methacrylate (e.g., amino-$C_2$-$C_{10}$ alkyl methacrylate) and one or more monomers of alkyl methacrylate (e.g., $C_2$-$C_{10}$ alkyl methacrylate). As used herein the term alkyl includes linear (unbranched) and branched carbon groups (chains) that may be saturated or unsaturated. As used herein the term amino includes —$NH_2$, —$NH(C_1$-$C_6)$alkyl, and —$NH((C_1$-$C_6))_2$alkyl. In one embodiment amino is —$NH_2$.

In one embodiment the membranolytic polymer is selected from the group consisting of poly(6-aminohexyl methacrylate) (PAHM), poly(aminoethyl-co-butyl methacrylate), poly(dimethylaminoethyl methacrylate-co-hexyl methacrylate), poly(benzyl amino acrylate/methacrylate), and poly(2-hexamethyleneimino)ethyl methacrylate. In one embodiment the membranolytic polymer is selected from poly($C_2$-$C_{10}$-alkyl guanidine) and poly(4-vinyl-N—($C_1$-$C_{10}$ alkyl pyridine). The membranolytic polymers described herein above in this paragraph are described in the following documents: (1) K. Kuroda, W. F. DeGrado, "Amphiphilic Polymethacrylate Derivatives as Antimicrobial Agents", J. Am. Chem. Soc. 2005, 127, 12, 4128-4129; (2) E. F. Palermo, K. Kuroda, "Chemical Structure of Cationic Groups in Amphiphilic Polymethacrylates Modulates the Antimicrobial and Hemolytic Activities", Biomacromolecules 2009, 10, 1416-1428; (3) E. F. Palermo, S. Vemparala, K. Kuroda, "Cationic Spacer Arm Design Strategy for Control of Antimicrobial Activity and Conformation of Amphiphilic Methacrylate Random Copolymers", Biomacromolecules 2012, 13, 1632-1641; (4) J. Piao, F. Gao, L. Yang, "Acid-Responsive Therapeutic Polymer for Prolonging Nanoparticle Circulation Lifetime and Destroying Drug-Resistant Tumors", ACS Appl Mater Interfaces 2016, 8, 1, 936-944; (5) N. H. Park, W. Cheng, F. Lai, et al. "Addressing Drug Resistance in Cancer with Macromolecular Chemotherapeutic Agents", J. Am. Chem. Soc. 2018, 140, 4244-4252; (6) G. Zhong, C. Yang, S. Liu, et al. "Polymers with Distinctive Anticancer Mechanism that Kills MDR Cancer Cells and Inhibits Tumor Metastasis", Biomaterials 2019, 199, 76-87; (6) H. Takahashi, K. Yumoto, K. Yasuhara, et al. "Anticancer Polymers Designed for Killing Dormant Prostate Cancer Cells. Sci. Rep. 2019, 9, 1096; (7) M. Luo, H. Wang, Z. Wang, et al. "A STING-Activating Nanovaccine for Cancer Immunotherapy", Nature Nanotechnol. 2017, 12, 648-654; (8) Y. Jiang, W. Zheng, L. Kuang, H. Ma, H. Liang, "Hydrophilic Phage-Mimicking Membrane Active Antimicrobials Reveal Nanostructure-Dependent Activity and Selectivity", ACS Infect. Dis. 2017, 3, 9, 676-687. The entire content of these documents (1-8) are hereby incorporated herein in their entirety.

In one embodiment the membranolytic polymer comprises one or more groups selected from amino, pyridine, guanidine, benzylamino, pyrrolidine, piperidine, and azepane.

In one embodiment the membranolytic polymer comprises monomers, wherein one or more of the monomers comprises one or more groups selected from amino, pyridine, guanidine, benzylamino, pyrrolidine, piperidine, and azepane. In one embodiment the membranolytic polymer comprises monomers wherein each monomer comprises one or more groups selected from amino, pyridine, guanidine, benzylamino, pyrrolidine, piperidine, and azepane.

In one embodiment the membranolytic polymer comprises one or more monomers selected from the group consisting of amino alkyl acrylate and amino alkyl methacrylate.

In one embodiment the membranolytic polymer is selected from the group consisting of poly(6-aminohexyl methacrylate) (PAHM), poly(aminoethyl-co-butyl methacrylate), poly(dimethylaminoethyl methacrylate-co-hexyl methacrylate), poly(benzyl amino acrylate/methacrylate), poly(2-hexamethyleneimino)ethyl methacrylate, poly($C_2$-$C_{10}$-alkyl guanidine), and poly(4-vinyl-N-alkyl pyridine).

In one embodiment the membranolytic polymer is not a protein. In one embodiment the membranolytic polymer is not a polypeptide. In one embodiment the membranolytic polymer does not comprise amino acids (e.g., natural and/or unnatural amino acids).

Shielding Polymer

As used herein the term "shielding polymer" refers to any polymer that associates with the membranolytic polymer. The shielding polymer can associate with the membranolytic polymer via different forces such as ionic, electrostatic and/or Van der Waals forces. The shielding polymer functions to decrease or eliminate the hemolytic and/or cytotoxicity properties of the membranolytic polymer when the shielding polymer is associated with membranolytic polymer. In one embodiment the shielding polymer is of opposite charge from the membranolytic polymer. Thus, the shielding polymer may be an anionic polymer.

In one embodiment the shielding polymer is an "anionic" polymer. Anionic polymers are polymers that have a negative charge. The negative charge is generally on the core structure of the anionic polymer with the functional group (moiety) bearing the negative charge (negatively charged group) covalently bonded to polymer. It is to be understood the negatively charged group will be associated with a positively charged counterion (such as positively charged group of a cationic polymer). In one embodiment the shielding polymer (e.g., anionic polymer) comprises one or more moieties selected from the group consisting of carboxylic acid, hydrogen sulfate, and sulfamic acid. Generally, the positively charged counterion will not be covalently bonded to the core of the shielding polymer (e.g., anionic polymer). In one embodiment the shielding polymer (e.g., anionic polymer) comprises one or more groups selected from the group consisting of carboxylic acid, hydrogen sulfate, and sulfamic acid. In one embodiment the shielding polymer (e.g., anionic polymer) comprises monomers, wherein one or more monomers comprise one or more negatively charged groups. In one embodiment the shielding polymer (e.g., anionic polymer) comprises monomers wherein each monomer comprises one or more negatively charged group. In one embodiment the shielding polymer (e.g., anionic polymer) comprises two or more repeat monomers. In one embodiment the shielding polymer (e.g., anionic polymer) is a homopolymer.

In one embodiment the shielding polymer (e.g., anionic polymer) is heparin. In one embodiment the shielding polymer (e.g., anionic polymer) is selected from the group consisting of Poly(L-glutamic acid) (PGLA, 3 k~15 k), Poly(acrylicacid) (PAA, 5.5 k), Poly(propylacrylic acid) (PPAA, 10 k), and hyaluronic acid (HA, 16.9 k).

In one embodiment the shielding polymer is not a protein. In one embodiment the shielding polymer is not a polypeptide. In one embodiment the shielding polymer does not comprise amino acids (e.g., natural and/or unnatural amino acids).

In one embodiment the ratio of membranolytic polymer to shielding polymer is about 1/1. In one embodiment the ratio of membranolytic polymer to shielding polymer is about 1/2. In one embodiment the ratio of membranolytic polymer to shielding polymer is about 1/4. In one embodiment the ratio of membranolytic polymer to shielding polymer is about 1/8.

One embodiment provides a composition comprising a membranolytic polymer or a salt thereof and a shielding polymer or a salt thereof provided the composition does not include a chemotherapeutic agent or a salt thereof.

One embodiment provides a composition, consisting essentially of a membranolytic polymer or a salt thereof and a shielding polymer or a salt thereof.

One embodiment provides a composition consisting of a membranolytic polymer or a salt thereof and a shielding polymer or a salt thereof.

Chemotherapeutic Agent

The term "chemotherapeutic agent" as used here is any agent (e.g., drug) that is useful for treating cancer. In embodiment the chemotherapeutic agent is a chemotherapeutic agent that is susceptible to efflux from a cancer cell by one or more efflux pumps. Examples of efflux pumps include P-gylcoprotein, MRP1, and ABCG2/BCRP.

In one embodiment the chemotherapeutic agent is an agent that is susceptible to efflux by P-Glycoprotein and/or MRP1 and/or ABCG2/BCRP (e.g., Doxorubicin, Daunorubicn, Epirubicin, Mitoxantrone, Viblastine, Vincristine, Etopside, Methotrexate, Paclitaxel, Camptothecin derivatives, SN-38, Topotecan, Flutamide, Hydroxyflutamide, Gefitinib).

In one embodiment the chemotherapeutic agent is an agent that is susceptible to efflux by P-Glycoprotein (e.g., Doxorubicin, Daunorubicn, Epirubicin, Mitoxantrone, Viblastine, Vincristine, Etopside, Methotrexate, Paclitaxel).

In one embodiment the chemotherapeutic agent is an agent that is susceptible to efflux by MRP1 (e.g., Doxorubicin, Daunorubicn, Epirubicin, Viblastine, Vincristine, Etopside, Methotrexate, Paclitaxel, Camptothecin derivatives, SN-38, Topotecan, Flutamide, Hydroxyflutamide).

In one embodiment the chemotherapeutic agent is an agent that is susceptible to efflux by ABCG2/BCRP (e.g., Doxorubicin, Daunorubicn, Mitotaxantrone, Methotrexate, Camptothecin derivatives, SN-38, Topotecan, Gefitinib).

In one embodiment the chemotherapeutic agent is doxorubicin (Dox).

In one embodiment the chemotherapeutic agent is an anthracycline or an alkylating agent.

Synergy

The term "synergy" refers to a combination of two or more agents wherein the activity of the combination of agents is greater than each individual agent and greater than the additive effect of each individual agent. The term synergistic effect or synergistic amount refers to an effect (e.g., biological activity) that displays synergy or an amount the displays synergy. Synergy can be calculated by known methods.

Nanoparticle

The term "nanoparticle" as used herein refers to particles of less than about 1 μm The compositions and combinations described herein can be formulated as nanoparticles. Such nanoparticles may reduce or attenuate toxicity (e.g., systemic toxicity) when administered to a mammal (e.g., a human). In one embodiment the nanoparticle has a diameter of less than 1 μm. In one embodiment the nanoparticle has a diameter of less than about 800 nm. In one embodiment the nanoparticle has a diameter of less than 500 nm. In one embodiment the nanoparticle has a diameter of less than about 200 nm.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compositions including pharmaceutical compositions described herein can comprise one or more excipients. When used in combination with the compositions (e.g., pharmaceutical compositions) described herein the term "excipients" refers generally to an additional ingredient that is combined the composition (e.g., pharmaceutical compositions) described herein to provide a corresponding composition. For example, when used in combination with the compositions (e.g., pharmaceutical compositions) described herein the term "excipients" includes, but is not limited to: carriers, binders, disintegrating agents, lubricants, sweetening agents, flavoring agents, coatings, preservatives, and dyes.

The compositions (e.g., pharmaceutical compositions) described herein can be administered to a mammalian host, such as a human patient in a variety of forms adapted to the chosen route of administration, i.e., orally or parenterally, by intravenous, intramuscular, topical or subcutaneous routes or intratumorally. For oral administration the compositions (e.g., pharmaceutical compositions) can be formulated as a solid dosage form with or without an enteric coating.

Thus, the present compositions (e.g., pharmaceutical compositions) may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, compositions (e.g., pharmaceutical compositions) may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied and may conveniently be between about 2 to about 90% of the weight of a given unit dosage form. The amount of active agents in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The compositions (e.g., pharmaceutical compositions) may also be administered intravenously or intramuscularly by infusion or injection. Solutions of the compositions (e.g., pharmaceutical compositions) can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compositions (e.g., pharmaceutical compositions) described herein in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compositions (e.g., pharmaceutical compositions) may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compositions (e.g., pharmaceutical compositions) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compositions (e.g., pharmaceutical compositions) and agents thereof required for use in treatment will vary with the route of administration, the nature of the condition being treated and the age and condition of the patient and will be ultimately at the discretion of the attendant physician or clinician.

In general, however, a suitable dose will be in the range of from about 1 to about 500 mg/kg, e.g., from about 5 to about 400 mg/kg of body weight per day, such as 1 to about 250 mg per kilogram body weight of the recipient per day.

The compound is conveniently formulated in unit dosage form; for example, containing 5 to 500 mg, 10 to 400 mg, or 5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention will now be illustrated by the following non-limiting Examples.

EXAMPLES

Example 1. A Membranolytic Polymer or a Salt Thereof (PAHM) and a Shielding Polymer or a Salt Thereof (Heparin)

Materials and Methods

Materials

Toluene (Sigma-Aldrich, St. Louis, Mo.) was dried by refluxing over sodium and distilled. N-(tert-butoxycarbonyl) aminohexyl methacrylate (tBocAHM) was synthesized as described by Zhu et al (C. H. Zhu, et al., Journal of Polymer Science Part a-Polymer Chemistry 48(13) (2010) 2869-2877]). Ethyl α-bromoisobutyrate, copper (I) chloride (CuCl), 2,2'-dipyridyl (bPy), and doxorubicin hydrochloride were purchased from Sigma-Aldrich. Maleic anhydride, dimethyl maleic anhydride, and citraconic anhydride were also ordered from Sigma-Aldrich. Cis-aconitic maleic anhydride was bought from Alfa Aesar (Ward Hill, Mass.). 2,4,6-trinitrobenzenesulfonic acid (TNBSA) was a product of Thermo Fisher Scientific Inc. (Rockford, Ill.). 3-[4,5-Dimethylthiazol-2-yl]-2,5-diphenyltetrazolium bromide (MTT), ethidium homodimer-1, Dulbecco's phosphate buffered saline (DPBS), Dulbecco's Modified Eagle's Medium (DMEM), fetal bovine serum (FBS), trypsin and HEPES buffer solution were purchased from Invitrogen (Carlsbad, Calif.). Other chemicals and solvents were purchased from Sigma-Aldrich and used without further purification.

Synthesis of poly (6-amino-1-hexyl methacrylate) (PAHM)

The atom transfer radical polymerization (ATRP) of tBocAHM followed the method reported by Ji et al (W. Ji, et al., Biomacromolecules 12(12) (2011) 4373-4385). Three different monomer/initiator feed ratios (20:1, 40:1, 100:1) were used to obtain poly (6-amino-1-hexyl methacrylate) (PAHM) homopolymers with varying molecular weights. For example, to synthesize PAHM with the largest degree of polymerization (DP), 1.0 g of tBocAHM, 6.8 mg of ethyl α-bromoisobutyrate, 3.5 mg of CuCl, 10.9 mg of bPy and 3 mL of dried toluene were added to a two-neck glass flask and degassed via three freeze-thaw cycles. The mixture was then heated at 80° C., stirred for 6 h. The reaction was terminated by exposing the system to air. The diluted reaction solution by dichloromethane was then passed through a basic aluminum oxide column to remove the copper complex. The resulting solution was concentrated under vacuum and precipitated in hexane twice and dried in vacuum at room temperature for 2 days. The Boc group was removed by dissolving 0.6 g of PtBocAHM in 5 mL of trifluoroacetic acid (TFA) and stirred for 2 h at room temperature. TFA was then removed by evaporation, and the residue was rinsed three times with diethyl ether. The resultant precipitate was collected by filtration, washed twice by diethyl ether, and dried overnight in vacuum. The polymers were then neutralized with 0.5 M NaOH water solution to reach pH 8.0, and dialyzed (MWCO 3,500) against distilled deionized water for 3 days. The final PAHM polymers were obtained by lyophilization. PtBocAHM with 20 targeting DP was recovered by removing most of solvents after eliminating the copper complexes. TFA was added directly to the above product, stirred for 2 h, and removed under vacuum. The residue was dissolved in water, neutralized with NaOH, dialyzed (MWCO 1,000), and lyophilized to harvest PAHM with the smallest DP. Poly (2-aminoethyl methacrylate) (PAEM) with DP100 was also synthesized by ATRP according to procedures by Ji et al.

Characterization of PAHM

The $^1$HNMR spectra of the polymers were acquired on a Varian Unity spectrometer (300 MHz) using $CDCl_3$ (for PtBocAHM) and $D_2O$ (for PAHM) as solvents. Chemical shifts were recorded in ppm and referenced against tetramethylsilane (TMS) and $D_2O$, respectively. Gel Permeation Chromatography (GPC) analysis of PtBocAHM was performed at 35° C. in $CHCl_3$ with a flow rate of 1 mL/min using a Hewlett-Packard 1100 series liquid chromatography equipped with three PL gel 5-μm mixed columns (Jordi Gel columns of 500, 103, and 104 Å pore sizes) and a Hewlett-Packard 1047A refractive index detector. The GPC instrument was calibrated with polystyrene standards (Polymer Laboratories, Amherst, Mass.). All sample solutions were filtered through a 0.22-μm filter before analysis.

Cytotoxicity in 2D Monolayer Cell Culture A mouse breast cancer cell line EMT-6 (ATCC, Manassas, Va.), two human breast cancer cell lines MDA-MB-231(ATCC) and MCF-7 (ATCC), and one human glioma cancer cell line T98G (ATCC) were used in standard MTT assays (T. Mosmann, J Immunol Methods 65(1-2) (1983) 55-63) to test the cytotoxicity of PAHM polymers with different molecular weight and concentration after 24 and 48 h of treatment. D ox-HCl was also tested for comparison. All of the four cancer cell lines were incubated in corresponding cell culture media, EMT-6 media (DMEM high glucose, 10% FBS, 100 U/mL penicillin/streptomycin), T98G and MDA-MB-231 media (DMEM low glucose, 10% FBS, 100 U/mL penicillin/streptomycin), MCF-7 media (DMEM low glucose, 10% FBS, insulin, 100 U/mL penicillin/streptomycin), at 37° C., and a humidified atmosphere containing 5% $CO_2$.

The MTT assay of PAHM polymers and Dox-HCl on EMT-6 cells exemplified the general experimental procedures. EMT-6 cells were seeded into 96-well plates at 5000 cells/well and cultured for 20 h in EMT-6 media at 5% $CO_2$ and 37° C. Afterwards polymers of various molecular weight and concentrations were added to the cells and cultured for 24 h or 48 h. MTT in PBS (5 mg/mL, 20 μL) was then added to each well, reaching a final concentration of 0.5 mg/mL. After 4 h, unreacted MTT was removed by aspiration. The formazan crystals were dissolved in 150 μL of DMSO, and the absorbance was measured at 570 nm using a Bio-Tek Synergy HT plate reader. Cell viability was calculated by [absorbance of cells exposed to polymers]/[absorbance of cells cultured without polymers] in percentage. Cell images were captured before MTT was added using an Olympus IX70 upright microscope under polarized light.

Cell Membrane Permeabilization by PAHM

EMT-6 cells were seeded into 96-well plates at 5000 cells/well and cultured for 20 h in EMT-6 media at 5% $CO_2$ and 37° C. The cells were washed by PBS and supplemented with 180 μL of fresh media for each well. Ethidium homodimer-1 solution in 20 μL of PBS was then added to above cells to reach a concentration of 4 μM and incubated for 10 min according to the manufacturer's instructions. PAHM polymers with three different chain lengths were added to cells pre-stained with ethidium homodimer-1 or cells without staining to reach 40 μg/mL and incubated for 10 min. Immediately, images of cells were captured by an Olympus IX70 inverted fluorescence microscope. Cells stained with ethidium homodimer-1 without PAHM treatment were used as controls.

Hemolysis

An eight-week old male C57BL/6 mouse was sacrificed by $CO_2$ asphyxiation and blood was collected from the heart and centrifuged at 1500 rpm for 5 min at 4° C. The plasma was removed, and the erythrocytes were resuspended in 2 ml ice cold PBS. The cells were again centrifuged at 1500 rpm for 5 min at 4° C. This procedure was repeated more than twice to ensure the removal of any released hemoglobin. After the supernatant was removed, the cells were resuspended in PBS solution and diluted to obtain a cell suspension with Abs=0.6 at 650 nm. PAHM and other samples were also diluted in PBS to reach different concentrations. 0.1 mL of the sample solutions were added to 0.1 mL of the RBC suspension in a 96-well plate and incubated for 1 h at 37° C. with mild shaking. Complete hemolysis was attained using a 2% v/v Triton-X yielding the 100% control value. PBS was used as negative control. After incubation, the 96-well plates were centrifuged at 1500 rpm for 5 min, and 100 μL of the supernatants were transferred to another 96 well plate. The release of hemoglobin was determined by UV at 414 nm. Each sample was measured in triplicates. Degree of hemolysis is defined as % lysis=100*($A_{polymer}$-$A_{blank}$)/($A_{triton}$-$A_{blank}$).

Formation and Particle Size Measurement of Heparin/PAHM Complex by Dynamic Light Scattering (DLS)

Heparin (sodium salt) was mixed with PAHM in 20 mM HEPES buffer (pH 7.4) and incubated for 30 minutes at room temperature. The charge ratio of heparin and PAHM was adjusted based on the assumption that one repeating unit of PAHM (Mw 325.88) bears 1 mole of positive charge (approximately the same number of primary amino groups) and that one repeating unit of heparin (Mw 1471) carries 8 moles of negative charges (approximately the number of carboxylate and sulfate groups combined). The final PAHM concentration was kept constant as 0.1 mg/mL. To determine the average particle size of the nano-complexes, the heparin/PAHM mixtures were diluted 20 times to a final volume of 2 mL in HEPES buffer. The average hydrodynamic diameter (or particle size) in HEPES buffer (20 mM) at 25° C. were determined using a ZetaPlus Particle Analyzer (Brookhaven Instruments Corporation, Holtsville, N.Y.; 27 mW laser; 658 nm incident beam, 90° scattering angle). Nano-complexes with heparin/PAHM charge ratios ranging from 1 to 32 were prepared as described above and measured by DLS.

The Effect of Heparin Complexation on Hemolytic Activity of PAHM

Heparin/PAHM complexes were prepared as shown above and diluted 10 times into saline buffer containing RBCs. The samples were incubated under 37° C. for 1 h with mild shaking, then centrifuged and 100 μL of the supernatant collected for measurement of hemoglobin concentration as described above.

Protamine disruption of heparin/PAHM complexation: hemolysis

To induce dissociation of heparin/PAHM, the nanoparticles prepared from charge ratio of 2 and PAHM concentration of 40 μg/mL was added to RBCs. Also added was protamine at the mass ratio of 8 (protamine/heparin), in large excess to heparin, in order to disrupt heparin/PAHM binding. Hemolysis was measured 2 and 24 h after protamine addition. Alternatively, protamine was incubated with heparin/PAHM nanoparticles for 24 h before adding to RBCs and the hemolysis assay was performed 24 h later. This is the 48 h time point measurement.

Protamine Disruption of Heparin/PAHM Complexation: Cancer Cell Killing

EMT-6 cells were treated with heparin/PAHM (charge ratio of 2) with the final PAHM concentration maintained as 20 μg/mL and 40 μg/mL. The nanoparticles were first added to the cells, followed by addition of protamine. Cell viability was measured using an MTT assay 24 h later. Protamine/heparin mass ratio was varying among 2, 4, 8.

In Vivo Tumor Model and Methods

Female 12-14-week-old Balb/C mice were inoculated with EMT-6 cells under the third nipple on the left flank. The mice were kept with constant access to food and water for 7 to 10 days until tumors became palpable with volumes of 100 mm$^3$ or larger and were randomized into groups of 3 to 8 mice. The mouse body weight was recorded, and the tumor length and width were measured using digital calipers. The mice were ear tagged for identification and tracking before treatments. The mice were monitored every day and the tumor sizes and mouse body weight were recorded every day. The tumor volume was calculated using the following equation [(length$^2$)×(width)]/2. At the end of experiments the mice were euthanized by $CO_2$ inhalation and the tumors were harvested, weighed and photographed.

Assessment of Anti-Tumor Effect of Nano-Formulated PAHM

The mice received a single injection through the tail vein on the first day of treatment and euthanized 4 to 8 days after treatment. The treatments include saline (negative control), various doses of heparin/PAHM complexes and equivalent doses of heparin alone. Free PAHM was also injected intratumorally for comparison. In all cases the dose of PAHM was kept constant at 20 mg/kg.

Results and Discussion

Synthesis and Characterization of PAHM Polymers

Most anti-cancer host defense peptides are cationic amphiphilic polymers which can bind to cancer cell membranes and cause cell death by destroying the membrane integrity (S. Al-Benna, Y. et al., Int J Mol Sci 12(11) (2011) 8027-8051). Synthetic polymers built with chemical structures containing certain positive charges and appropriate hydrophobic components can also have strong interaction with cell membranes (K. Kuroda, et al., J Am Chem Soc 127(12) (2005) 4128-4129). The structure of PAHM was chosen for sufficiently dense cationic primary amines to bind to cell surface and for appropriate hydrophobicity to disrupt cell membrane. PAHM was used as a copolymer with PDMAEMA to bind and deliver plasmid DNA to cells within its nontoxic concentration (C. H. Zhu, et al., Journal of Polymer Science Part a-Polymer Chemistry 48(13) (2010) 2869-2877). While biocompatibility is important for a polymer to be a good candidate for gene delivery application, cytotoxicity of a polymer may be good to kill cancer cells. Here PAHM homopolymers were synthesized and their capability was exploited to kill cancer cells both in vitro and in vivo to show the possibility that synthetic polymers can be a new class of anticancer agent.

PAHM homopolymers were synthesized via a controlled radical polymerization technique, ATRP, which offers a convenient and effective means to generate polymers with well-defined chain-length, composition, and molecular architecture (K. Matyjaszewski, et al., Chem Rev 101(9) (2001) 2921-2990). In the first step, ethyl α-bromoisobutyrate was used to initiate the ATRP of the Boc-protected 6-amino-1-hexyl methacrylate (tBocAHM) to give PtBocAHM. The molar ratio of tBocAHM monomer and the initiator was varied from 20, 40 to 100 to achieve three PtBocAHM with monomer conversions of 95%, 98% and 99% respectively (determined by proton NMR, data not shown) and yield of over 70%. The average degree of polymerization (DP) of the PtBocAHM was calculated to be 18, 38, and 100 based on monomer conversion, and the three polymers were thus named PtBocAHM$_{18}$, PtBocAHM$_{38}$, and PtBocAHM$_{100}$, respectively. GPC traces showed single peaks and the number-average molecular weight (Mn) of the three polymers was calculated to be 0.82×10$^4$, 1.20×10$^4$, and 2.08×10$^4$ with the polydispersity index (PDI) of 1.13, 1.18, and 1.23, respectively. Monomodal and symmetric GPC peaks along with narrow molecular weight distribution indicated that well-defined PtBocAHM by ATRP were obtained successfully. In the second step, the Boc-protecting group was completely removed from PtBocAHM by acid treatment, yielding the final products of PAHM. The ease of synthesis and availability of a large number of structurally diverse monomers would enable further optimization of cytotoxicity and specificity.

PAHM Kills 2D Monolayer Cells Effectively

Figure 4:
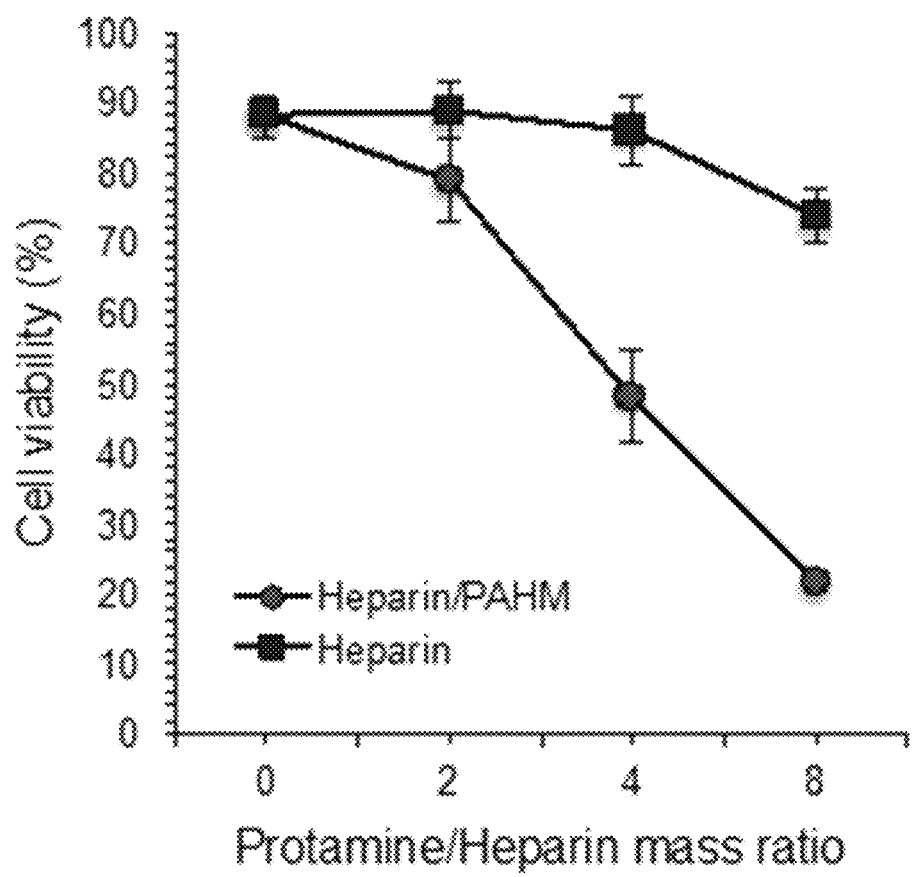
FIG. 4 shows released PAHM from heparin nanoparticles regains cancer cell killing activity.

To determine the cytotoxicity of PAHM, murine EMT-6, three human cancer cell lines MDA-MB-231, MCF-7, and T98G were treated for 24 and 48 hours with varying concentrations and measured cell viability by MTT assay. A widely used chemo drug doxorubicin was also used as a control to compare the potency of PAHM to kill cancer cells. For the three PAHM polymers with varying chain lengths, there's no significant difference among their capacities to kill these 4 cancer cell lines in most cases. PAHM maintained its cytotoxicity even with 18 repeating units, whose chain length was in the similar range with those of many anticancer peptides (S. Al-Benna, et al., Int J Mol Sci 12(11) (2011) 8027-8051). The potency of PAHM to kill EMT-6 and MDA-MB-231 in 2D monolayer culture was similar to Dox. After 24 h treatment by PAHM and Dox, the IC$_{50}$ of the PAHM and Dox were close around 10-15 μg/mL in EMT-6 and MDA-MB-231, as shown in FIGS. 4.2A & 4.2B. 48 h later, the IC$_{50}$ of Dox decreased to 5 μg/mL while IC$_{50}$ of PAHM didn't change much. Longer treatment time induced smaller IC$_{50}$ of Dox could be attributed to more cellular accumulation of Dox to cause more apoptosis. PAHM showed superior potency to Dox in killing multidrug resistant cells MCF-7 and T98G (M. Mohri, et al., J Neurooncol 49(2) (2000) 105-115; L. Rieger, et al., Acta Neuropathol 99(5) (2000) 555-562.). After 24 h treatment by PAHM and Dox, the IC$_{50}$ of the PAHM was around 10-15 μg/mL in MCF-7 and T98G cells, while IC$_{50}$ of Dox were 30 μg/mL and far above 40 μg/mL respectively. Increasing treatment time to 2 days did not alter the IC$_{50}$ values of PAHM polymers, but did decrease the gap of IC$_{50}$ values between the PAHM and Dox. These 2D monolayer cytotoxicity data imply that PAHM kill cancer cells via a mechanism different from Dox, which may be a benefit to overcome the multi-drug resistance of cancer cells.

PAHM Kills Cells Through Membrane Lysis

PAHM's cationic and amphiphilic chemical structure, along with non-selective cytotoxicity between regular and multi-drug resistant cells remind us that PAHM and most anti-cancer host defense peptides may share similar mechanism to kill cancer cells through cell membrane disruption. Thus, a fluorescent dye ethidium homodimer-1(EthD-1) was selected to evaluate plasma membrane integrity after PAHM treatment. EthD-1 can undergo a 40-fold enhancement of fluorescence upon binding to nucleic acids when it enters cells with damaged membranes, while EthD-1 is excluded by the intact plasma membrane of live cells (E. S. Kaneshiro, et al., 17(1) (1993) 1-16). Thereby, there is a bright red fluorescence coming out in dead cells after EthD-1 staining, but not live cells. Rapid EMT-6 cell death due to membrane permeation was observed even after only 10 min exposure to PAHM, no matter how large the polymer was. And few red fluorescence signals were found in the control group, which justified the validity of this assay. The bright field images of EMT-6 cells were also recorded 10 min after PAHM treatment. EMT-6 showed round, swollen morphology, which was distinguished from control cells. The above dye permeation experiment suggested strong membrane lytic activity of PAHM as the mechanism of cell killing. Cancer cells may not be able to develop resistance to this rapid cell killing by PAHM.

Hemolysis experiment also confirmed the capability of PAHM to lyse cell membranes. Longer PAHM has slightly higher hemolytic ability than shorter ones. At 80 µg/mL, all PAHM polymers induced around 90% red blood cell lysis.

Nano-Complex Formation: Dependence of Charge Ratio

As a cationic polymer, PAHM was expected to form polyelectrolyte complex with anionic polymers such as heparin. Indeed, at 1:1 charge ratio and beyond, PAHM and heparin formed complexes with average particle size around 120 nm or smaller (FIG. 1). At charge ratio greater than 4, there was a significant reduction in particle size, suggesting that the excess negatively charged heparin was able to condense and compact the cationic PAHM, rather than simple association. In the presence of large excess of heparin (charge ratio 16 and above), it was possible that PAHM reached maximum compaction, which explained that fact the particle size did not change anymore.

Heparin Complexation Abolishes the Hemolytic Activity of PAHM

Figure 2:
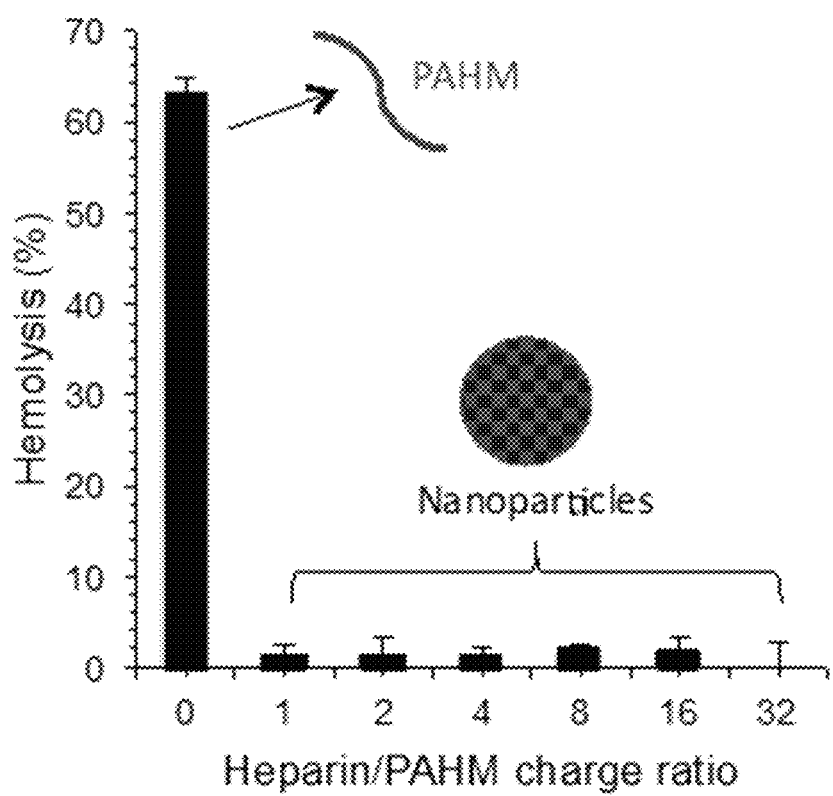
FIG. 2 shows heparin complexation abolishes the hemolytic activity of PAHM.

While free PAHM at 20 µg/mL caused over 60% RBC lysis in 24 h, the same concentration of PAHM in the form of heparin complexation (or nanoparticles) had negligible degree of hemolysis (starting with charge ratio of 1 and beyond) (FIG. 2). One possible explanation is that heparin neutralizes the cationic charges of the PAHM, disrupting its interaction with the membrane of RBCs. This finding confirms the validity of using heparin complexation as a means to reduce toxic side effect of PAHM, which would allow for safe, systemic administration.

Released PAHM from Heparin Nanoparticles Regains Hemolytic Activity

Figure 3:
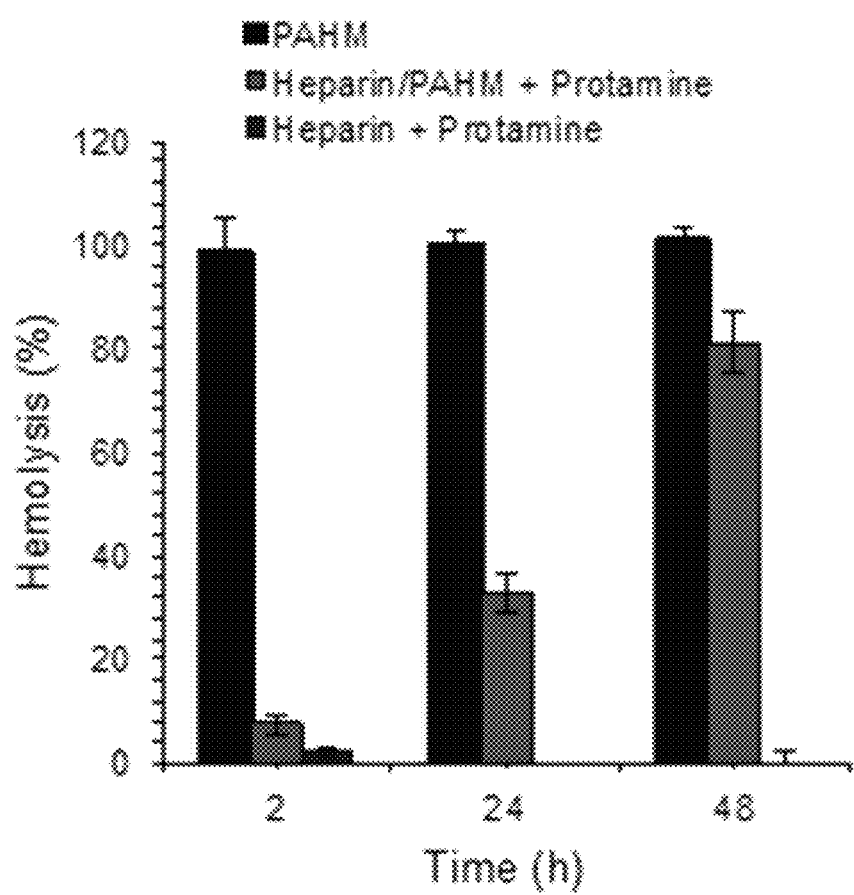
FIG. 3 shows released PAHM from heparin nanoparticles regains hemolytic activity. First bar in each set is PAHM, second bar in each set is Heparin/PAHM+Protamine, and the third bar in each set is Heparin+protamine.

Free PAHM at 40 µg/mL was extremely hemolytic, essentially lysing all RBCs. When complexed, however, the heparin/PAHM nanoparticles were completely not hemolytic (FIG. 3). Yet, in the presence of excess amount of protamine, hemolytic activity of the complexes recovered as time went by. These results suggest that protamine treatment effectively broke up the heparin/PAHM nanoparticles, freeing up the PAHM, ready to engage with cellular targets.

Released PAHM from Heparin Nanoparticles Regains Cancer Cell Killing Activity

Protamine solutions were prepared with the increasing protamine/heparin ratios (2, 4, 6, 8). The heparin/PAHM nanoparticles were first treated with protamine solutions and then added to EMT-6 cells. As more protamine was presence, it was easier for the nanoparticles to be disrupted, releasing free PAHM that increased cancer cell death. The observation holds true for two doses of PAHM: 20 (FIG. 4) and 40 µg/mL (not shown).

Other Anionic Polymers

The principle of heparin-mediated nano-formulation of PAHM should apply to other, but not all, anionic polymers. For examples, albumin carries net negative charges and has been used extensively as a nanocarriers for drugs. It was found that bovine serum albumin (BSA) only weakly binds to PAHM without forming stable nanoparticles and fails to abolish the cytotoxicity of PAHM (data not shown). The following anionic polymers: Poly(L-glutamic acid) (PGLA, 3 k~15 k), Poly(acrylic acid) (PAA, 5.5 k), Poly(propylacrylic acid) (PPAA, 10 k), and hyaluronic acid (HA, 16.9 k) were also studied. These anionic polymers are only a selected few, chosen for their origin (synthetic and natural) and proven record of biocompatibility. All of these anionic polymers could form complexes with PAHM resulting in particles of various sizes ranging from nano to micro scale. They all reduced, sometimes abolished, hemolytic and cytotoxic activities of the PAHM in complexed form (data now shown). It is possible that the most desirable set of properties of the ideal anionic polymer for this approach may include: formation of stable nano or micrometer size particles in aqueous media, effective abolishment of hemolytic and cytotoxic activities of PAHM, and moderate complexation with PAHM which allows for reversal of complexation in vivo to regain cytotoxic activity in cancer cells. Heparin is one such anionic polymer that fulfills all these requirements.

Figure 5A:
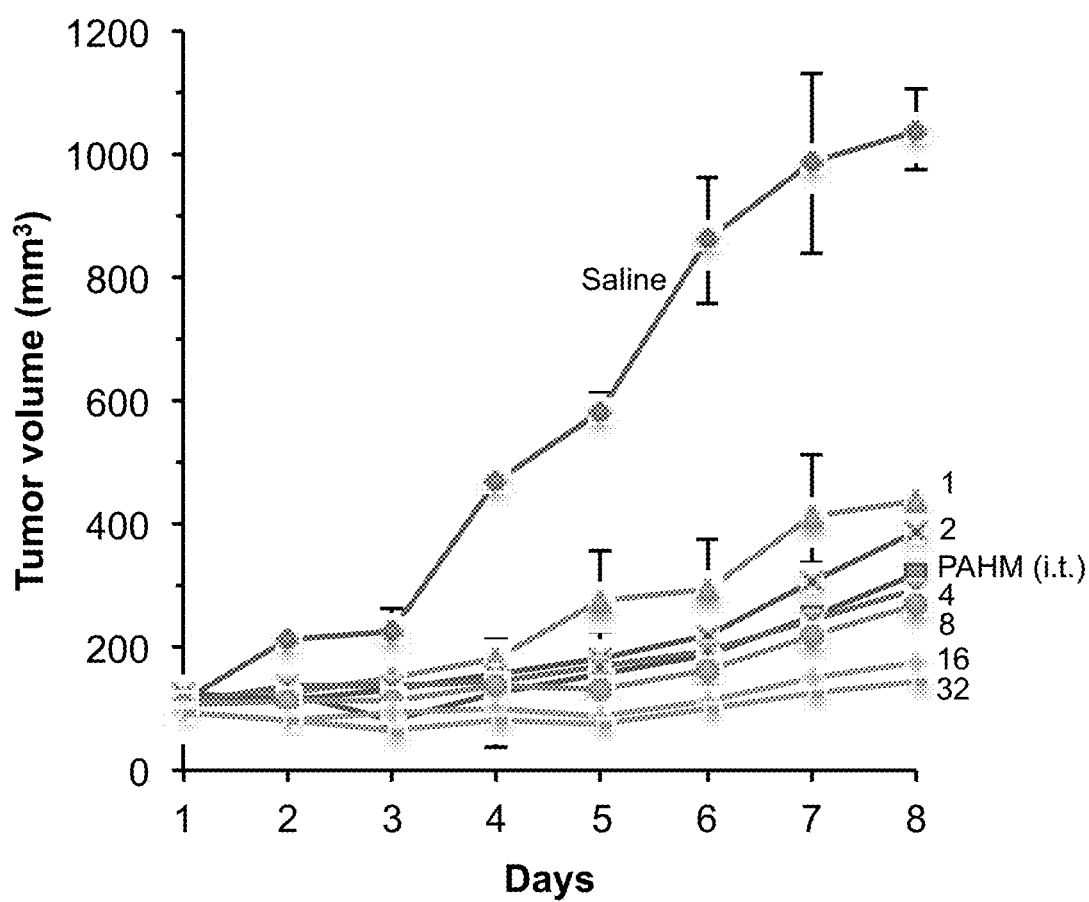
FIGS. 5A-5D show Heparin/PAHM nanoparticles suppress tumor growth after a single systemic administration with constant body weight.
Figure 5B:
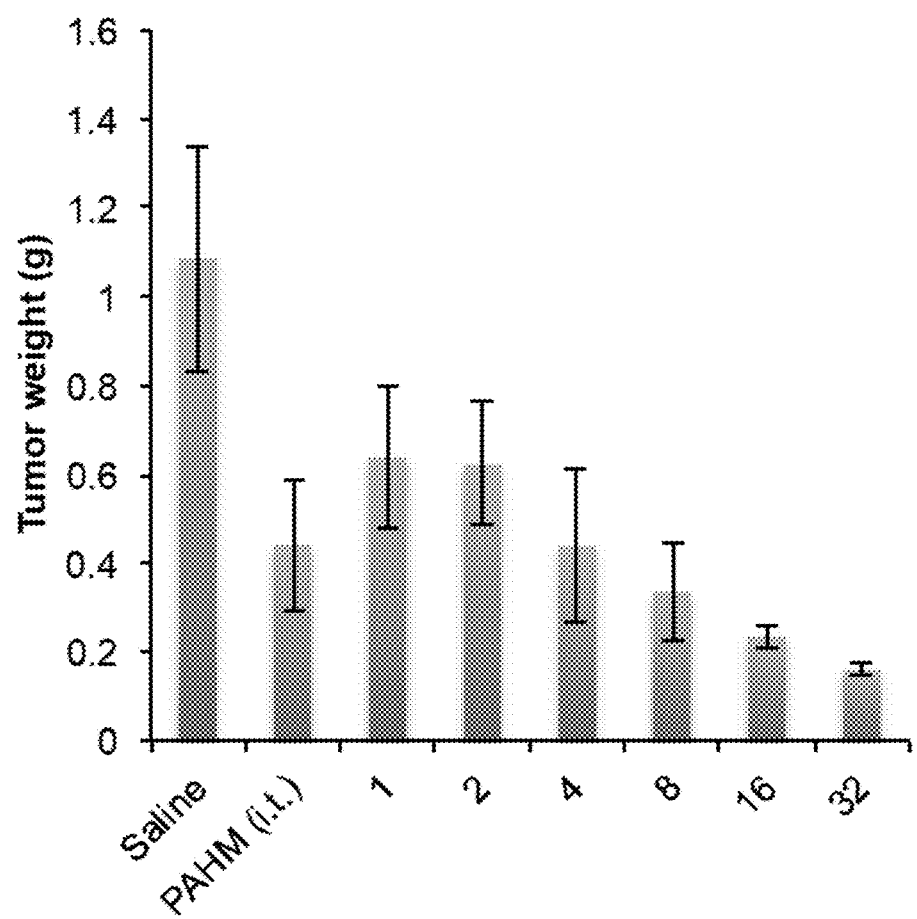
Figure 5C:
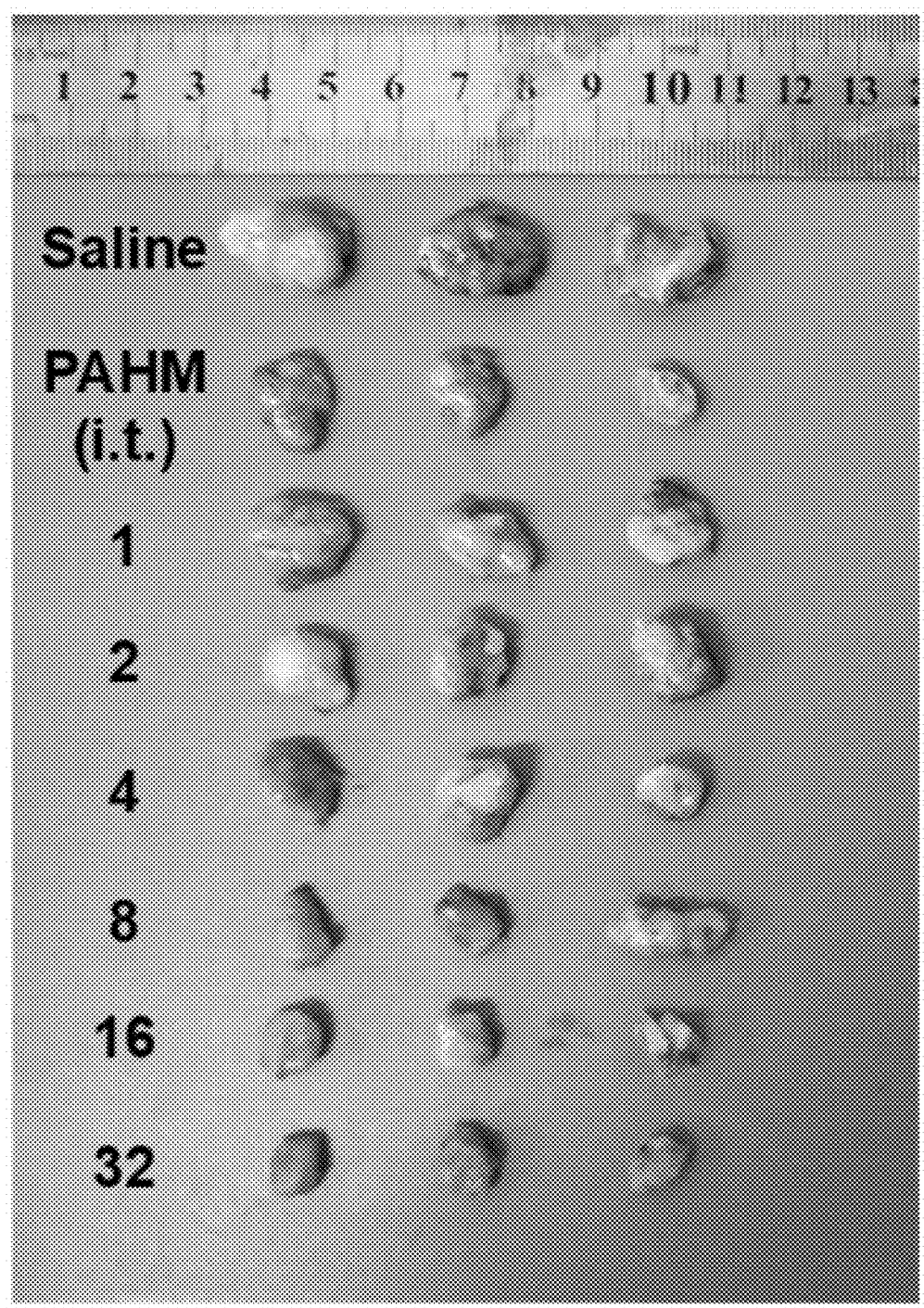
Figure 5D:
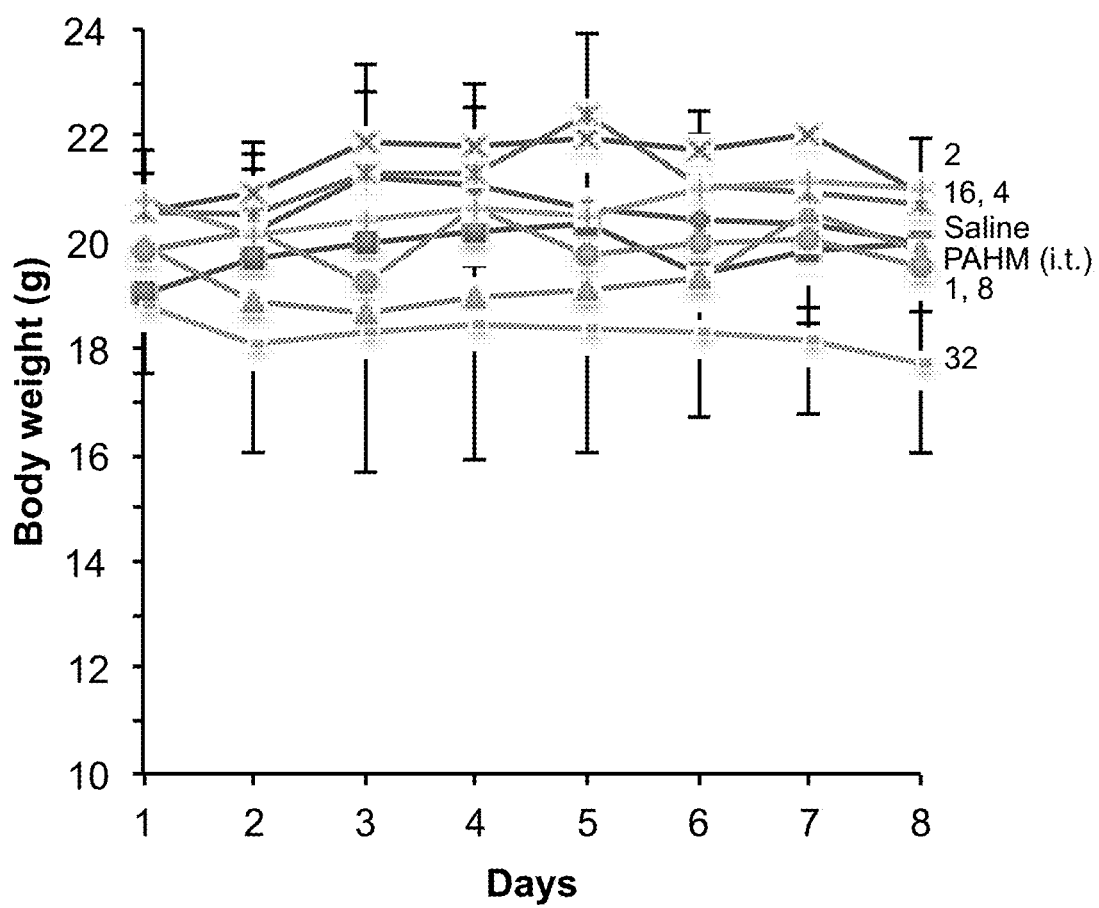

Heparin/PAHM Nanoparticles Suppress Tumor Growth after a Single Systemic Administration In comparison with saline control, significantly reduced tumor growth was observed for a single i.v. administered treatment of heparin/PAHM nanoparticles with various charge ratios from 1 to 32 (FIGS. 5A, 5B, and 5C). Higher heparin/PAHM charge ratio appeared more effective in suppressing tumor growth. Although intratumorally injected PAHM was somewhat effective in reducing tumor size, free PAHM cannot be injected intravenously unless complexed with heparin. Heparin/PAHM nanoparticles showed no apparent systemic toxicity judging from the constant body weight of mice throughout the treatment (FIG. 5D).

The Anti-Tumor Effect of Heparin/PAHM is Robust and not Due to Heparin Alone

Figure 6A:
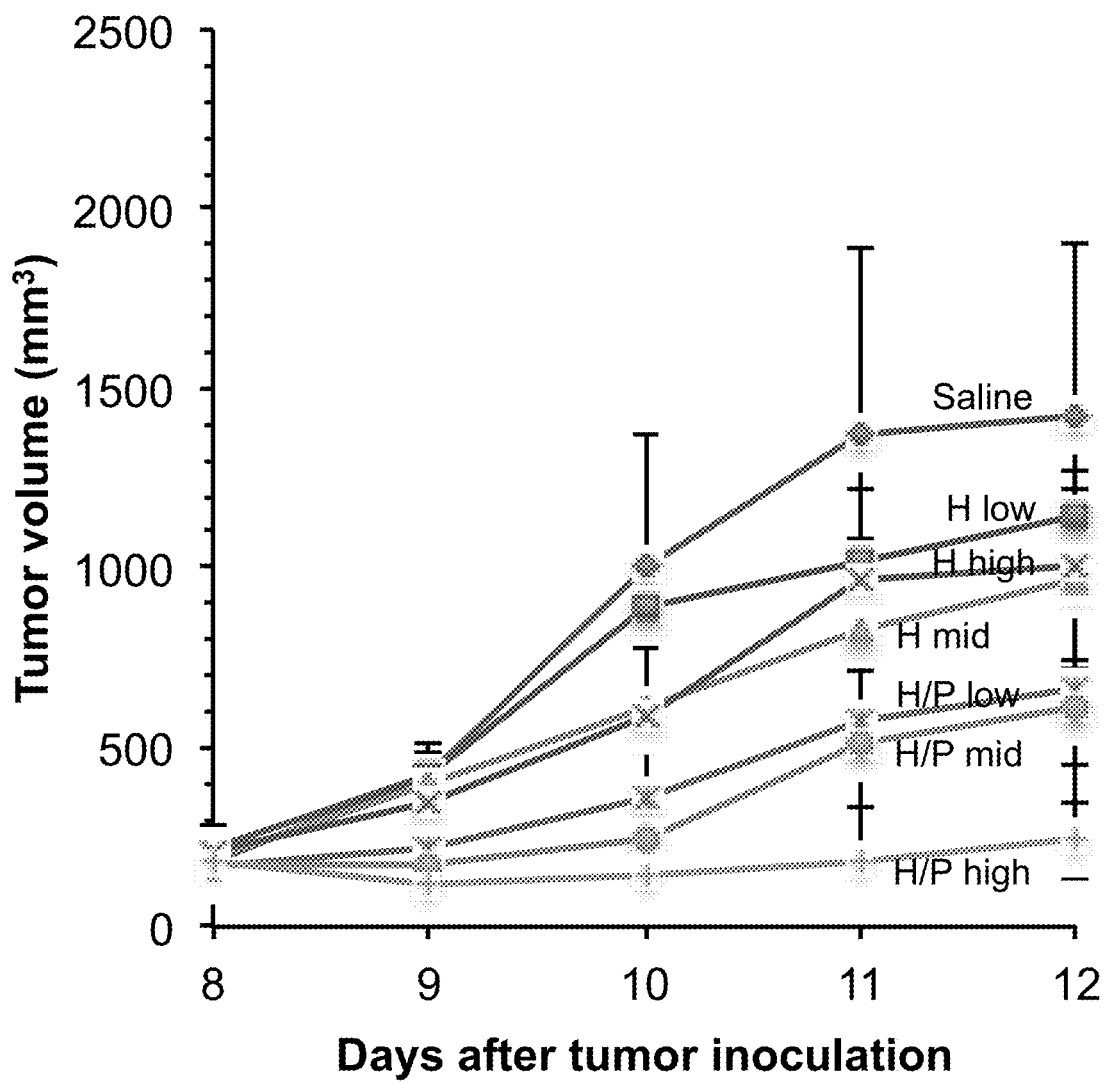
FIGS. 6A-6E show the anti-tumor effect of heparin/PAHM at selected charge ratios (1, 4, 16) in a mouse study (8 mice per group) with no significant influence on body weight. The treatment groups receiving increasing doses of heparin are represented as "low, med, high".
Figure 6B:
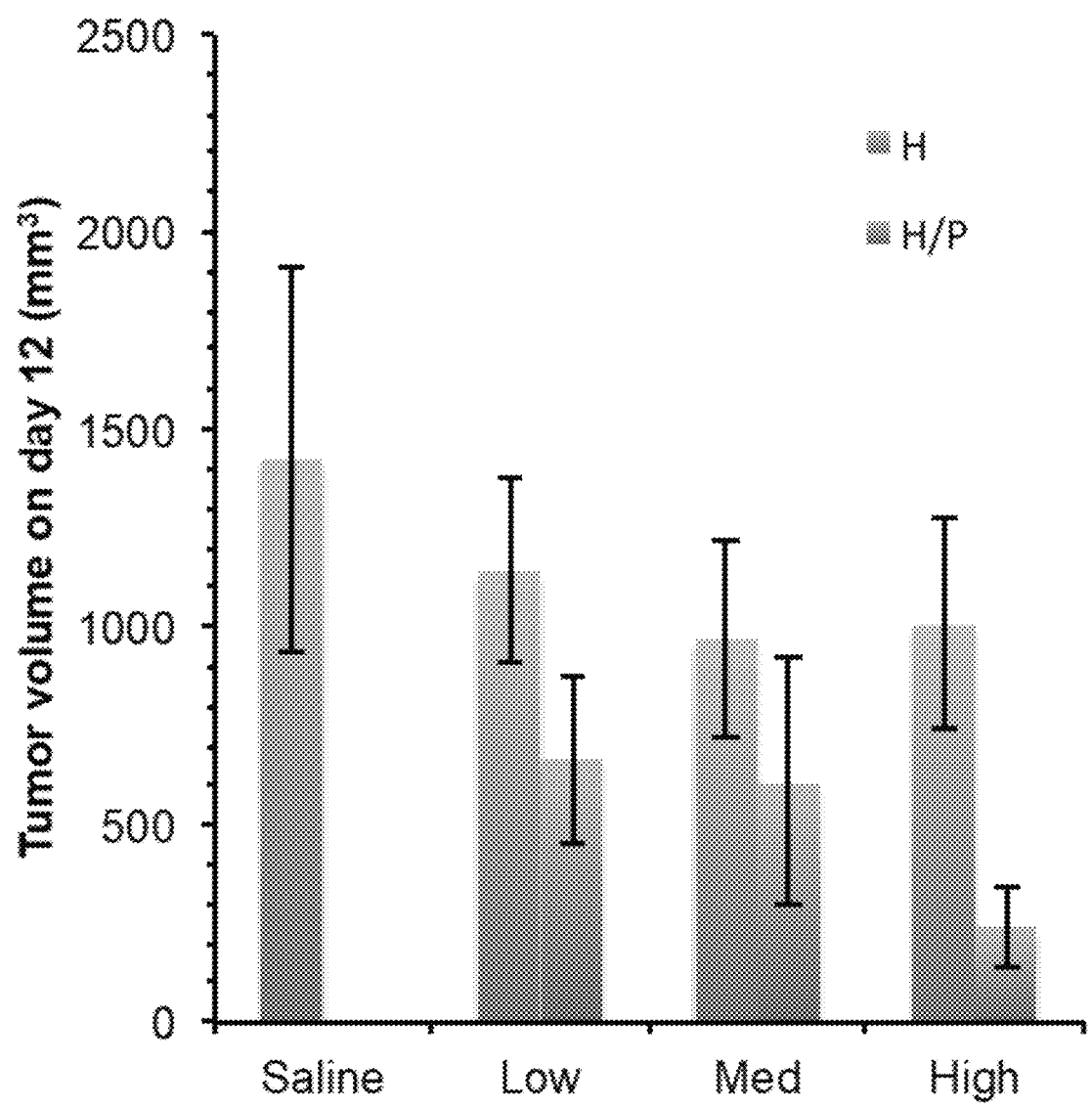
Figure 6C:
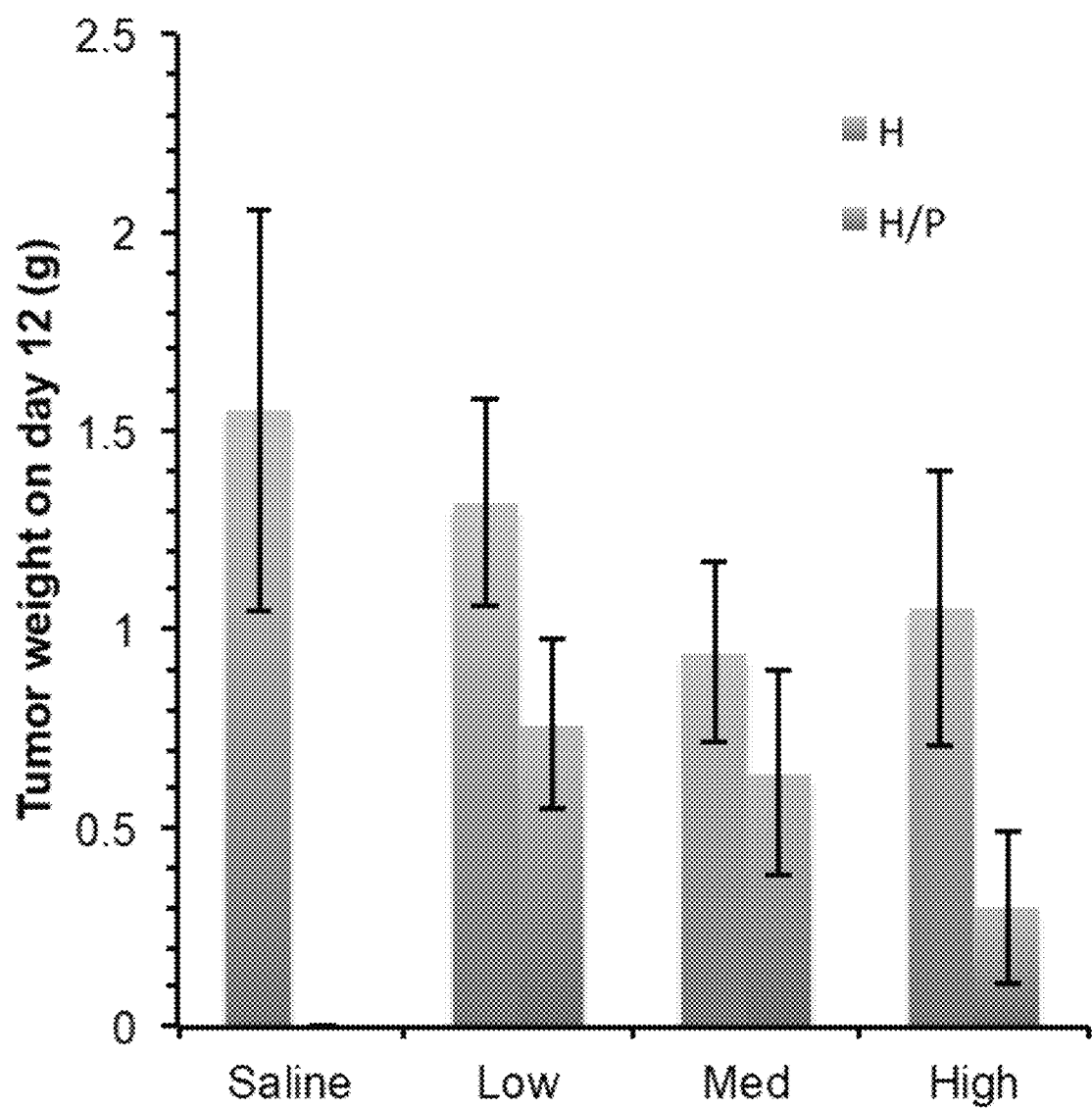
Figure 6D:
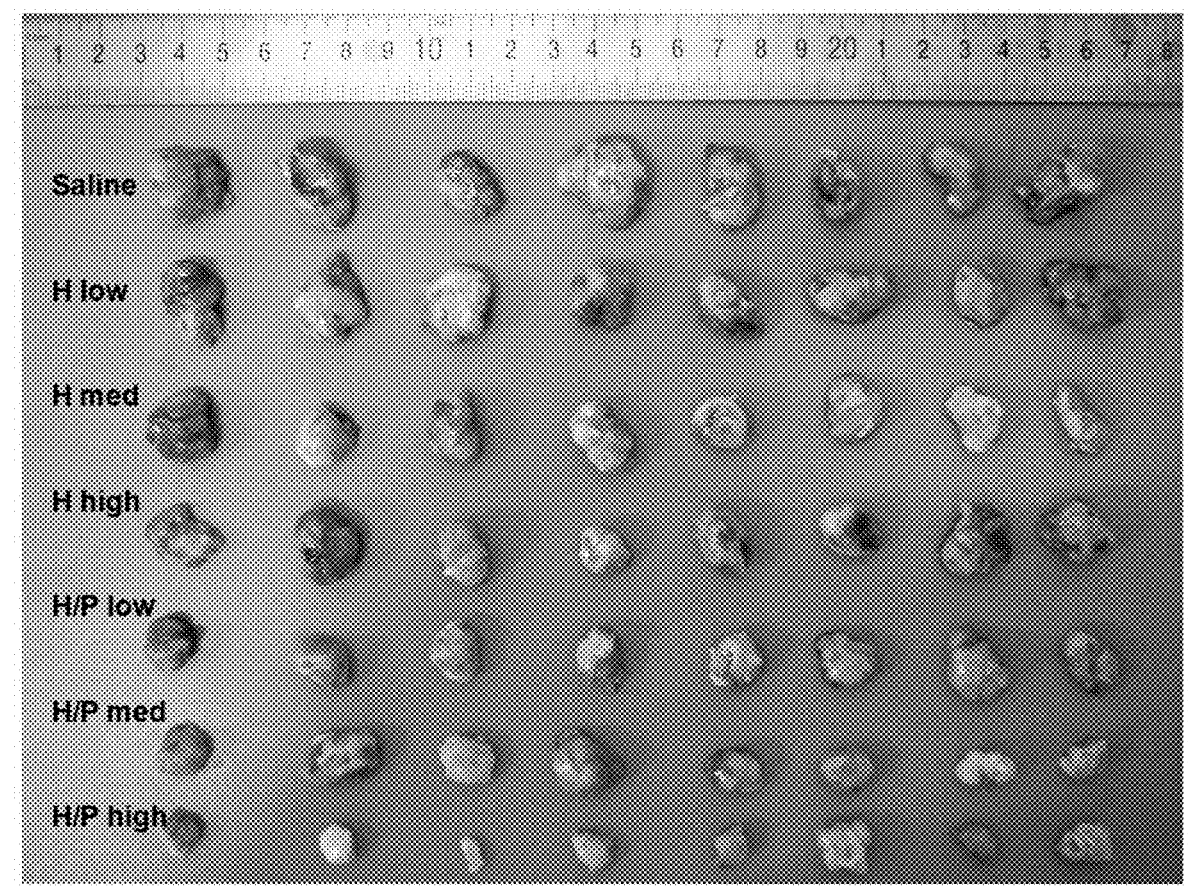
Figure 6E:
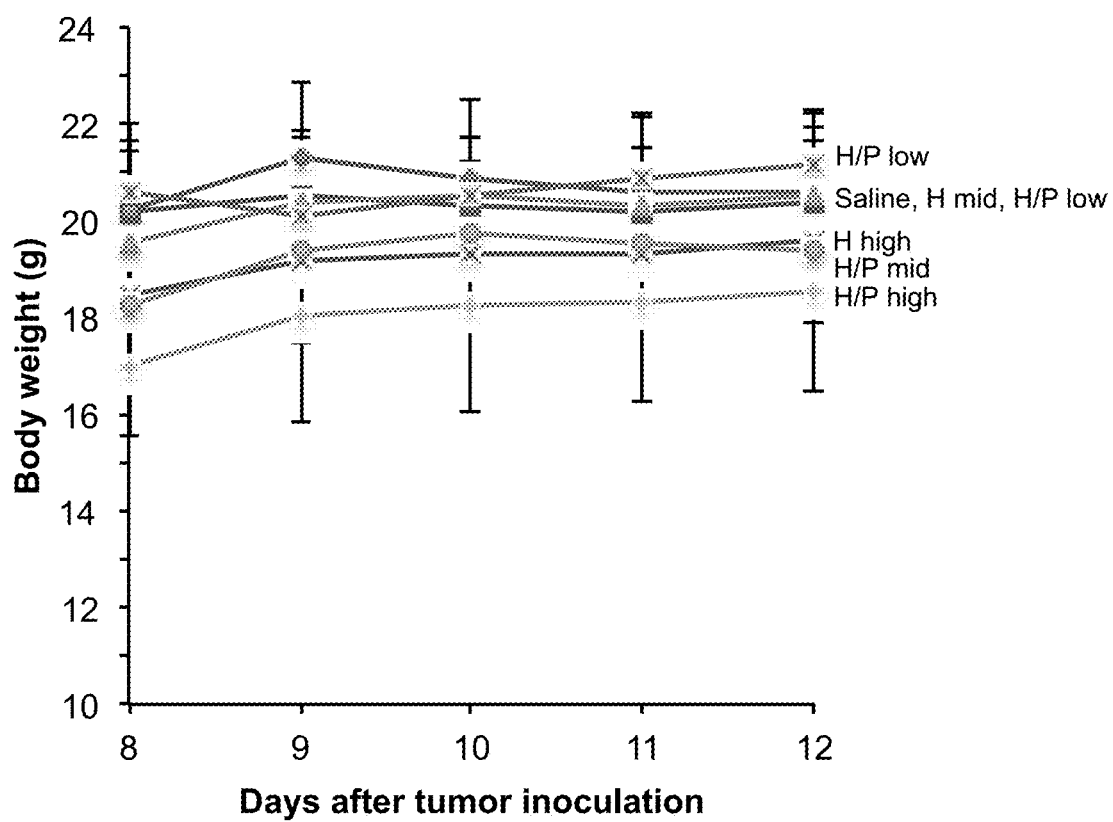

The anti-tumor effect of heparin/PAHM at selected charge ratios (1, 4, 16) was verified in a larger scale experiment (8 mice per group) (FIGS. 6a. 6B, and 6C). The treatment groups receiving increasing doses of heparin are represented as "low, med, high". From individual tumor growth curves and average tumor volume and weight results it's clear that the heparin/PAHM nanoparticles at all three doses, especially the high-dose treatment, had therapeutic effect. Heparin treatment alone had modest but insignificant effect on tumor growth (FIG. 6D). No significant influence on mouse body weight was found.

Example 2. A Membranolytic Polymer or a Salt Thereof (PAHM) and a Chemotherapeutic Agent Experimental Methods Culture of Cells Mouse breast mammary carninoma cells (EMT6, ATCC® CRL-2755™) and human pancreatic adenocarcinoma cells (AsPC-1, ATCC® CRL-1682™) were grown in RPMI 1640 medium supplemented with 10% heat inactivated fetal bovine serum (FBS), penicillin (100 U/mL) and streptomycin (100 µg/mL). Cells were grown in 75 cm$^2$ polystyrene tissue culture flasks and incubated at 37° C., 5% CO$_2$, 95% relative humidity. Every 3-4 days, cells were passaged and reseeded at 2.25×10$^5$ cells/flask (EMT6) or 1.5×10$^6$ cells/flask (AsPC-1).

PAHM Membrane Permeation (EMT6)

EMT6 cells were plated at 5000 cells/well (in 200 µL medium) in a 96-well plate. After culturing overnight (18 h), the medium was removed, cells were washed twice with 200 µL phosphate buffered saline (PBS), and 180 µL phenol red free medium was added to the cells along with 20 µL propidium iodide solution (40 μM in PBS; final concentration: 4 μM PI). Poly (6-amino-1-hexyl methacrylate) (PAHM) was dissolved in phenol red free medium and 20 was added to the EMT6 cells for the following final concentrations: 10 μg/mL, 20 μg/mL, 30 μg/mL, 40 μg/mL.

EMT6 cells were imaged with a widefield fluorescent microscope (Nikon Eclipse Ti-E Inverted Miscroscope System equipped with an Andor Zyla sCMOS Camera and controlled by NIS Elements Software) using a 40× (0.6 NA) objective. Cells were imaged with phase contrast (exposure time: 200 ms) and propidium iodide was imaged with a TRITC fluorescent filter with single band exciter ($\lambda_{ex}$: 515/30 nm, $\lambda_{em}$: 590/45 nm, exposure time: 200 ms). Timelapse microscopy was performed for 30 min in a controlled environment (37° C., 5% $CO_2$, 95% relative humidity), acquiring images every 25 sec. Images were analyzed in FIJI.

PAHM Membrane Permeation and Doxorubicin Uptake (AsPC-1)

AsPC-1 cells were plated at 1×10$^5$ cells/dish (in 2 mL medium) in 35 mm glass bottom microwell dishes. After culturing overnight, the medium was removed, cells were washed twice with 1 mL PBS, and 2 mL live cell imaging solution (LCIS) was added to the cells. Cell nuclei were stained by adding two drops of NucBlue® Live Ready-Probes® Reagent (Hoechst 33342), followed by 20 min incubation. PAHM and doxorubicin hydrochloride (Dox) were dissolved in LCIS and 200 μL was added the AsPC-1 cells for the following final concentrations: 5 μg/mL Dox, 5 μg/mL Dox+5 μg/mL PAHM, 10 μg/mL Dox, 10 μg/mL Dox+10 μg/mL PAHM. Cells were incubated for 15 minutes before the Dox and/or PAHM solutions were removed, cells were washed twice with 1 mL PBS, and 2 mL LCIS was added to the cells.

AsPC-1 cells were imaged with a widefield fluorescent microscope (Olympus IX70 Inverted System Microscope equipped with an Olympus DP72 Microscope Digital Camera and controlled by cell Sens Standard Software) using a 20× (0.45 NA) objective. Cells were imaged phase contrast (exposure time: 10 ms), stained nuclei were imaged with a DAPI/Hoechst/AMCA filter ($\lambda_{ex}$=350/50 nm, $\lambda_{em}$=460/50 nm, exposure time: 10 ms), and Dox was imaged with a TRITC (Rhodamine)/Di1/Cy3 filter ($\lambda_{ex}$=535/50 nm, $\lambda_{em}$=610/75 nm, exposure time: 100 ms). Images were analyzed in FIJI and Dox uptake was quantified using CellProfiler.

PAHM+Dox Cytotoxicity Assay

AsPC-1 or EMT6 cells were plated at 5000 cells/well (in 100 μL phenol red free medium) in 96-well plates. After culturing overnight (~20 h), the medium was removed, and 100 μL medium containing various concentrations of PAHM and/or Dox was added to the cells. AsPC-1 cells were exposed to 1-100 μg/mL PAHM, 1-100 μg/mL Dox, or combinations of PAHM and Dox at a 1:1 ratio. EMT6 cells were exposed to 1-100 μg/mL PAHM, 0.02-2 μg/mL Dox, or combinations of PAHM and Dox at a 50:1 ratio. After 24 h exposure, the PAHM and Dox solutions were removed and 100 μL phenol red free medium was added to the cells. Cell viability was measured using an MTT assay. To each well, 10 μL MTT solution (12 mM in PBS) was added. After 4 h, 85 μL was removed from each well and formazan was solubilized in 100 μL dimethyl sulfoxide (DMSO). Absorbance was measured at 540 nm using a plate reader (BioTek™ Cytation™ 3 Cell Imaging Multi-Mode Reader controlled by Gen5™ All-In-One Microplate Reader Software). Data was analyzed in Microsoft Excel and Combination Indices and Dose Reduction Indices were calculated using CompuSyn (ComboSyn, Inc.)

Statistical Analyses

Statistical analyses were performed by one-way ANOVA and Tukey HSD test for multiple comparisons. Values are shown as means±SD.

Results and Discussion

PAHM Membrane Permeation (EMT6)

Figure 7:
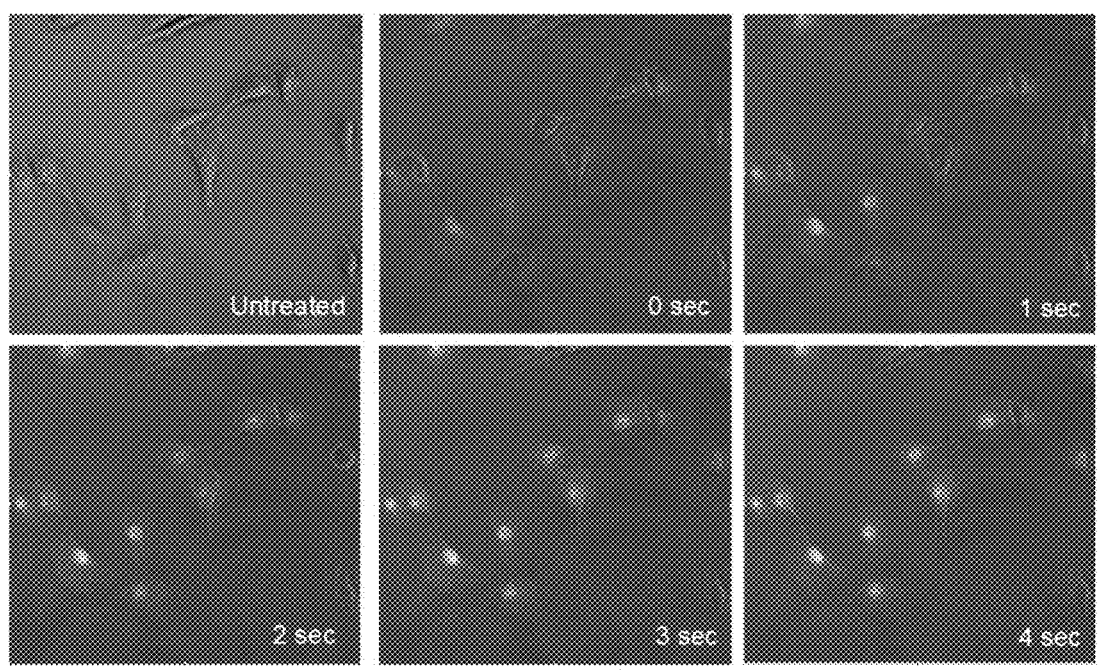
FIG. 7 shows that permeation of EMT6 cell membranes is noticeable immediately after the addition of PAHM (mouse breast cancer cells (EMT), propidium iodide (PI) (4 µM), PAHM 10 µg/mL added at 0 seconds).

Permeation of EMT6 cell membranes is noticeable immediately after the addition of PAHM (FIG. 7). Cells begin to round-up and swell due to the leaky membranes. This is also evident by the influx of propidium iodide. Normally cell-membrane impermeable, propidium iodide enters the cells after PAHM addition and binds to DNA. When bound to DNA, the propidium iodide fluorescence is enhanced 20- to 30-fold, and the fluorescence excitation and emission maxima is shifted ~30-40 nm and ~15 nm, respectively. This can be seen in the time-lapse microscopy immediately after PAHM addition.

PAHM Membrane Permeation and Doxorubicin Uptake (AsPC-1)

Figure 8:
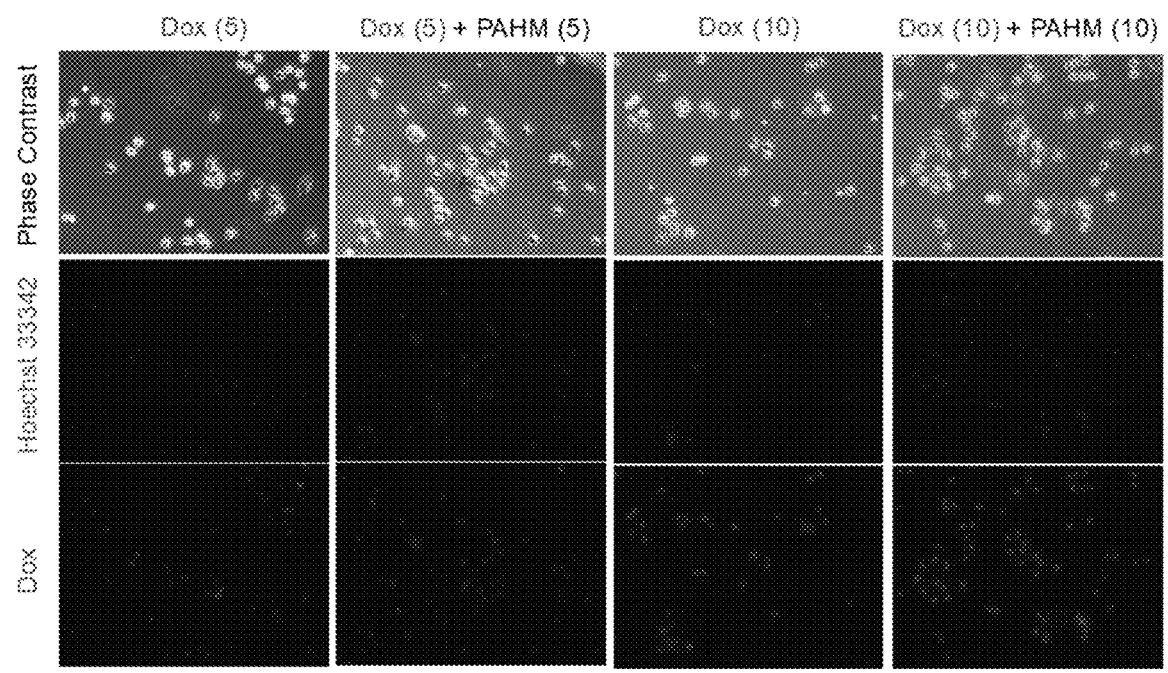
FIG. 8 shows the permeation of AsPC-1 cell membranes by PAHM can also increase uptake of Dox (15 minutes).

Permeation of AsPC-1 cell membranes by PAHM can also increase uptake of Dox (FIG. 8). Normally subject to efflux pumps, Dox can enter the cells due to the membrane permeation by PAHM and accumulate in the nuclei. can be seen by the increased fluorescence intensity (red channel: Dox) in the cells treated with 10 μg/mL PAHM+10 μg/mL Dox as compared to 10 μg/mL Dox alone. However, the phenomenon is not shown at lower drug concentrations, as there is no difference in fluorescence intensity between 5 μg/mL PAHM+5 μg/mL Dox and 5 μg/mL Dox alone. This concentration dependence seems to agree with the cytotoxicity data. Analysis of the combination index shows that Dox and PAHM become synergistic at total concentrations of 20 μg/mL (10 μg/mL PAHM+10 μg/mL Dox) and above.

PAHM+Dox Cytotoxicity Assay

Figure 9A:
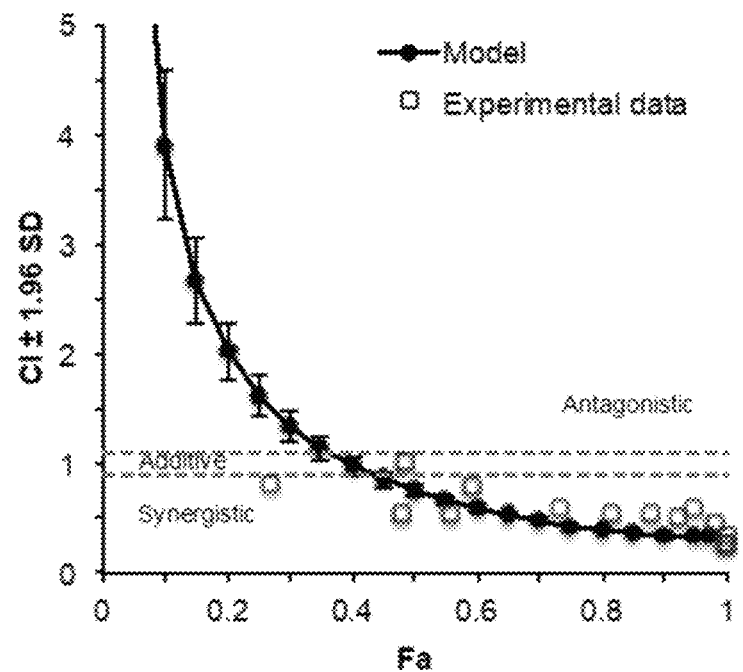
FIG. 9A shows the combination of PAHM and Dox is more effective at killing EMT6 cells in an MTT assay.
Figure 9B:
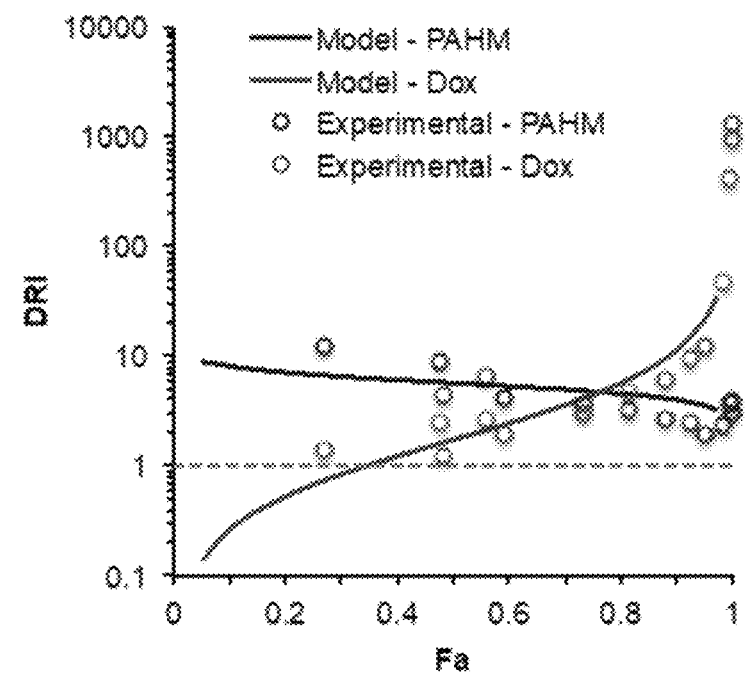
FIG. 9B shows that Dose Reduction Index (DRI) for PAHM and Dox when used in combination. All DRI values are above 1, suggesting that the dose of each therapeutic agent can be reduced when used in combination. The top line of data points is the theoretical DRI for PAHM, and the bottom line of data points is the theoretical DRI. The top series of empty circles is the experimentally determined DRI for PAHM and the bottom series of empty circles is the experimentally determined DRI for Dox.
Figure 10A:
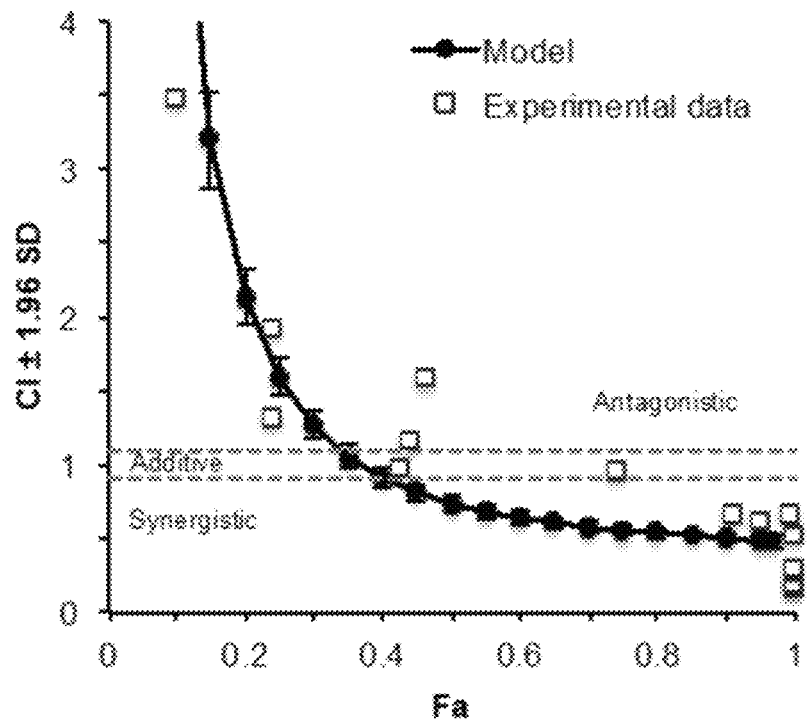
FIG. 10A shows the combination of PAHM and Dox is more effective at killing AsPC-1 cells in an MTT assay.
Figure 10B:
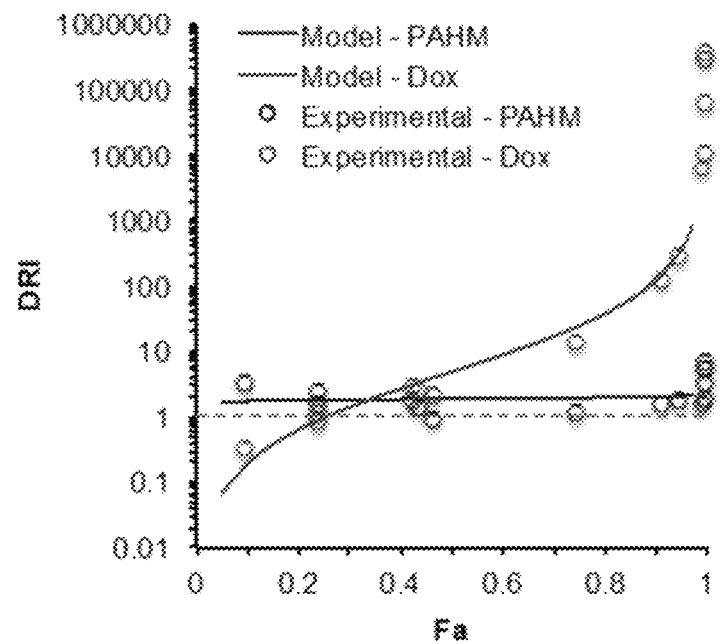
FIG. 10B shows that Dose Reduction Index (DRI) for PAHM and Dox when used in combination. All but one DRI values are above 1, suggesting that the dose of each therapeutic agent can be reduced when used in combination. The top line of data points is the theoretical DRI for PAHM, and the bottom line of data points is the theoretical DRI. The top series of empty circles is the experimentally determined DRI for PAHM and the bottom series of empty circles is the experimentally determined DRI for Dox.

MTT assay shows combination of PAHM and Dox is more effective at killing both EMT6 cells (FIG. 9A) and AsPC-1 cells (FIG. 10A) than PAHM or Dox alone. At a fractional affect greater than 0.4 (i.e., 60% cell viability), the combination is synergistic as shown by combination index (CI)<0.9 (FIG. 9B for EMT6 cells and FIG. 10B for AsPC-1 cells). The combination can also reduce the dose of either PAHM or Dox to achieve than same fractional affect. However, Dox benefits much more than PAHM from the combined use as seen by the much higher Dose Reduction Indices (DRI) for Dox than PAHM.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition comprising:
   A membranolytic polymer or a salt thereof, and a shielding polymer or a salt thereof, provided the composition does not include a nucleic acid;
   wherein the membranolytic polymer is poly(6-amino-hexyl methacrylate) (PAHM) or a salt thereof; and
   the shielding polymer is heparin.

2. The composition of claim 1 that is formulated as a nanoparticle.

3. The composition of claim 1 further comprising a pharmaceutically acceptable excipient.

4. A method to treat cancer in mammal in need thereof comprising administering to the mammal a composition as described in claim 1.

5. The composition of claim 1 further comprising a chemotherapeutic agent or a salt thereof.

6. The composition of claim 5, wherein the membranolytic polymer and the chemotherapeutic agent are provided in synergistic amounts and wherein the membranolytic polymer and chemotherapeutic agent are present in the composition as separate compounds.

7. The composition of claim 5, wherein the chemotherapeutic agent is an agent that is susceptible to efflux by P-Glycoprotein and/or MRP1 and/or ABCG2/BCRP.

8. The composition of claim 5, wherein the chemotherapeutic agent is selected from the group consisting of Doxorubicin, Daunorubicin, Epirubicin, Mitoxantrone, Viblastine, Vincristine, Etopside, Methotrexate, Paclitaxel, Camptothecin derivatives, SN-38, Topotecan, Flutamide, Hydroxyflutamide, and Gefitinib.

* * * * *